United States Patent [19]

Akopov et al.

[11] 4,216,890
[45] Aug. 12, 1980

[54] SURGICAL APPARATUS FOR SUTURING ORGANS WITH METAL STAPLES

[76] Inventors: Ernest M. Akopov, Dubninskaya ulitsa, 61, kv. 88; Petr M. Postolov, Sadovo-Triumfalnaya ulitsa, 4/10, kv. 105, both of Moscow, U.S.S.R.

[21] Appl. No.: 957,991

[22] Filed: Nov. 6, 1978

[51] Int. Cl.² .............................................. A61B 17/00
[52] U.S. Cl. ......................................... 227/22; 227/19
[58] Field of Search .................... 29/466, 469, 812; 128/325, 334, 337; 227/19, 22, 25, 30, 135, 152

[56] References Cited

U.S. PATENT DOCUMENTS 3,973,709  8/1976  Akopov et al. ................... 227/19

Primary Examiner—Paul A. Bell
Attorney, Agent, or Firm—Lackenbach, Lilling & Siegel

[57] ABSTRACT

A surgical apparatus for suturing organs with metal staples comprises two clamps, each of said clamps having two jaws for clamping and fixing the organs being sutured and detachably joined together so that the mating plane of the jaws of each clamp is perpendicular to the mating plane of the clamps. Mounted on the clamp jaws are magazines with slots for staples, staple pushers, dies with grooves for clinching said staples and suitable for grasping and fixing the walls of the organs being sutured, embodied as casings with members fixing the walls of the organs. The casings are set on each of the jaws in guides permitting restricted movement of said casings in a plane perpendicular to the mating plane of the jaws and the mating plane of the clamps. Locks are mounted on said jaws locking the casings in the forward position, and said locking members lie between the mating surface of said clamp jaws and at some distance in front of the mating surfaces of said clamps, and locks locking the casings in the backward position, lie at some distance from the mating surfaces of the clamp jaws and approximately in the mating planes of the clamps and retain said casings regardless of the reciprocal positions of the clamps and the width of the suturing clearance between the magazines and the dies.

17 Claims, 67 Drawing Figures

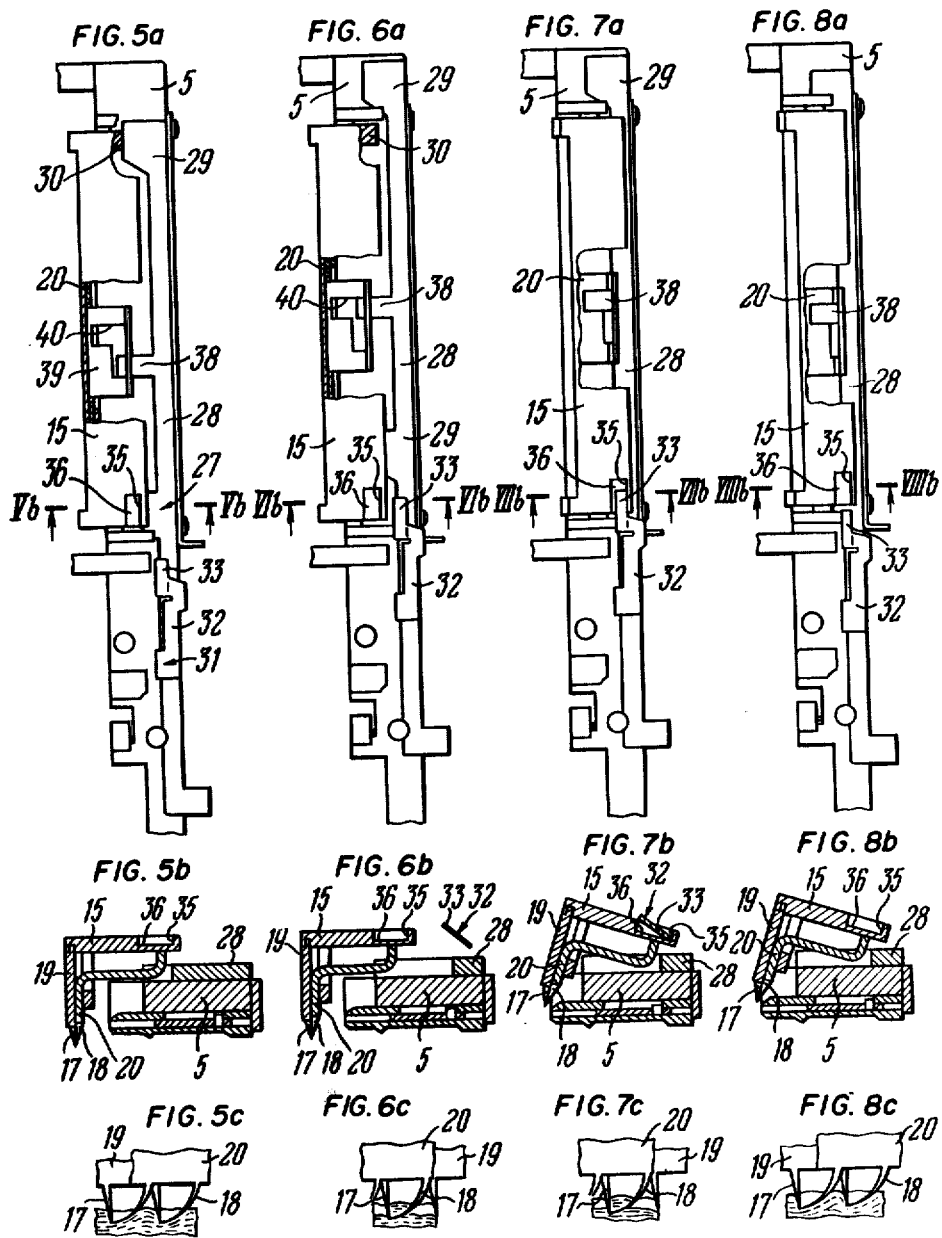

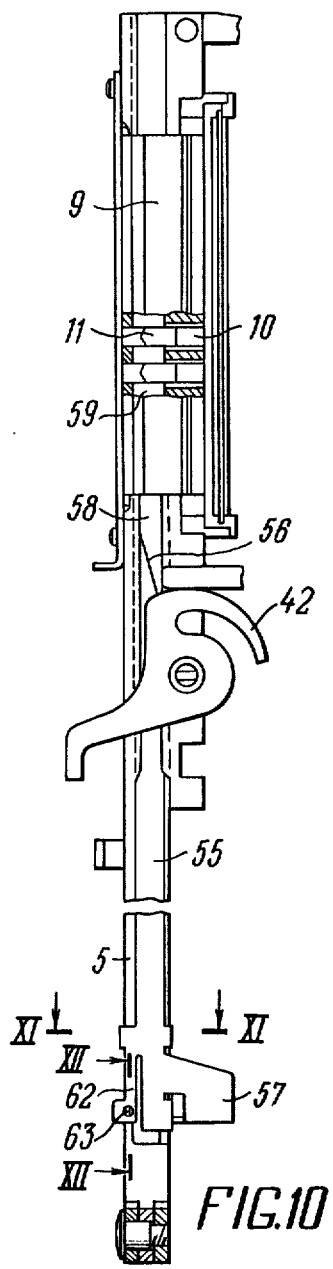
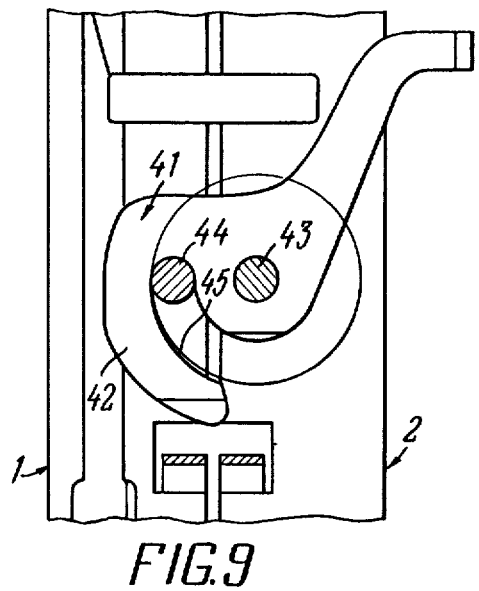
FIG.9
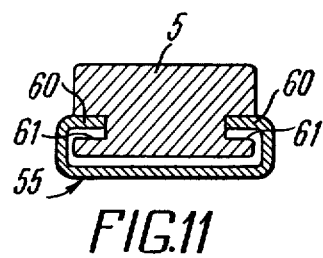
FIG.11
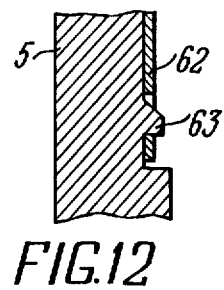
FIG.12
FIG.10

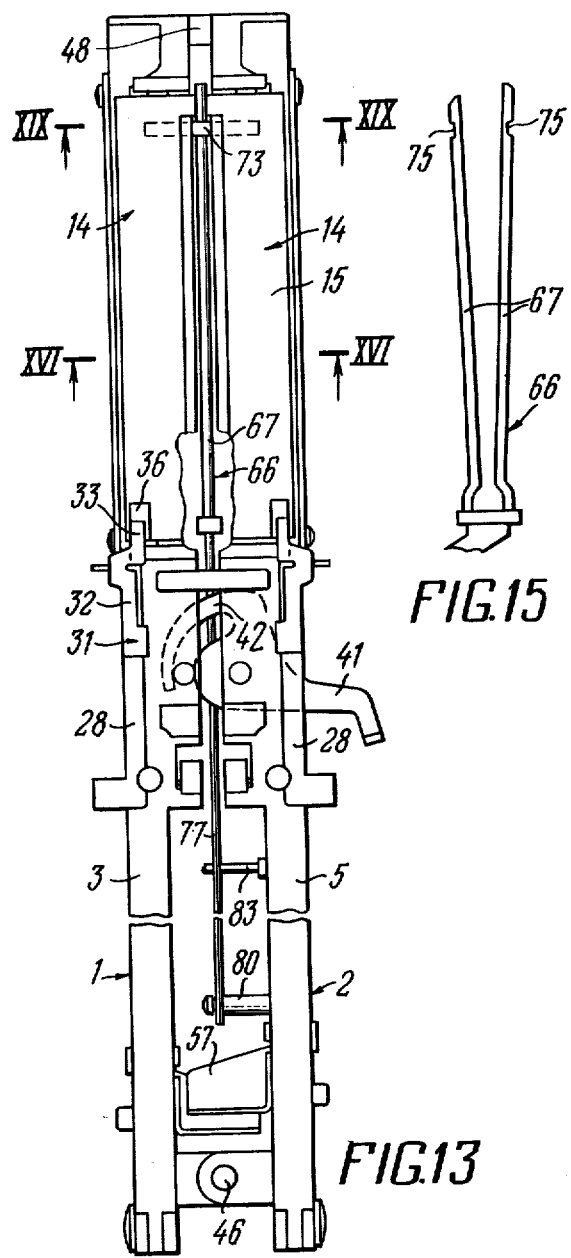
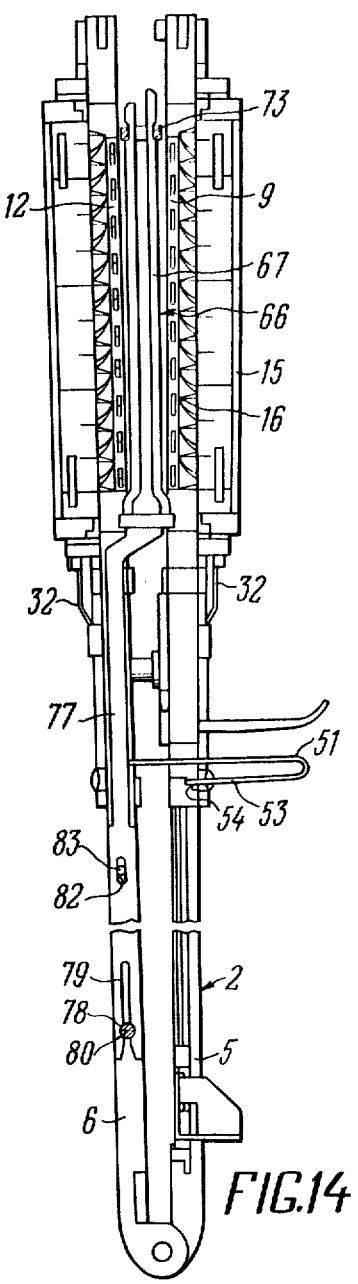
FIG.13   FIG.14   FIG.15

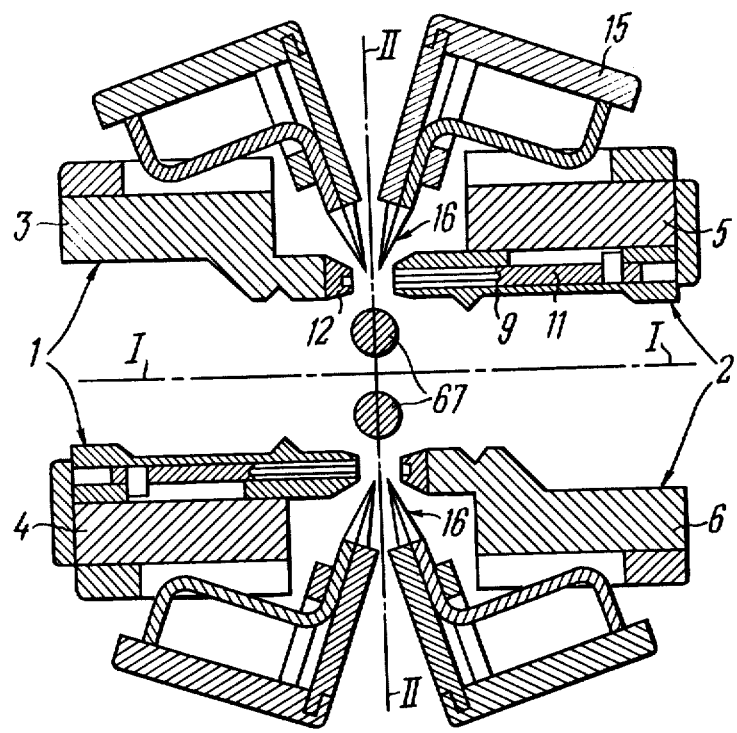

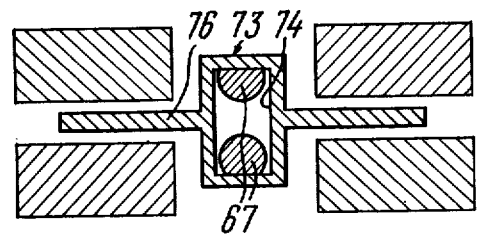
FIG.19
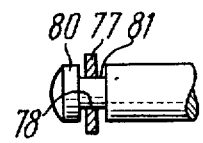
FIG.20
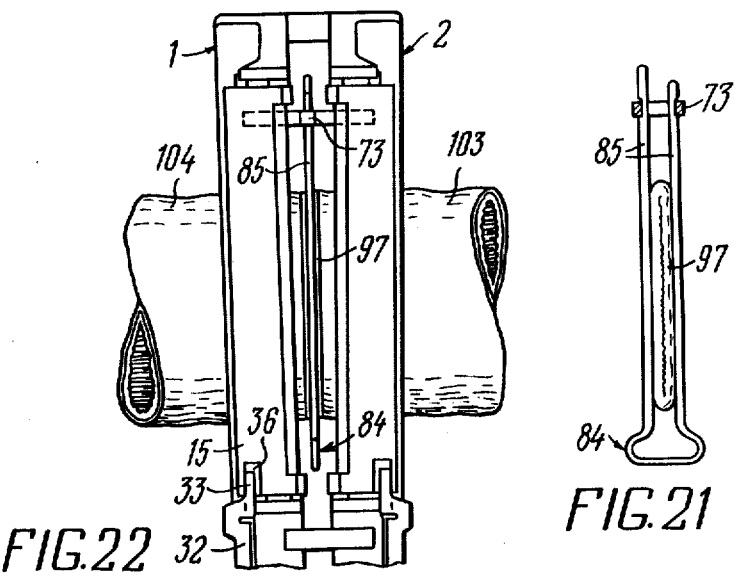
FIG.21
FIG.22

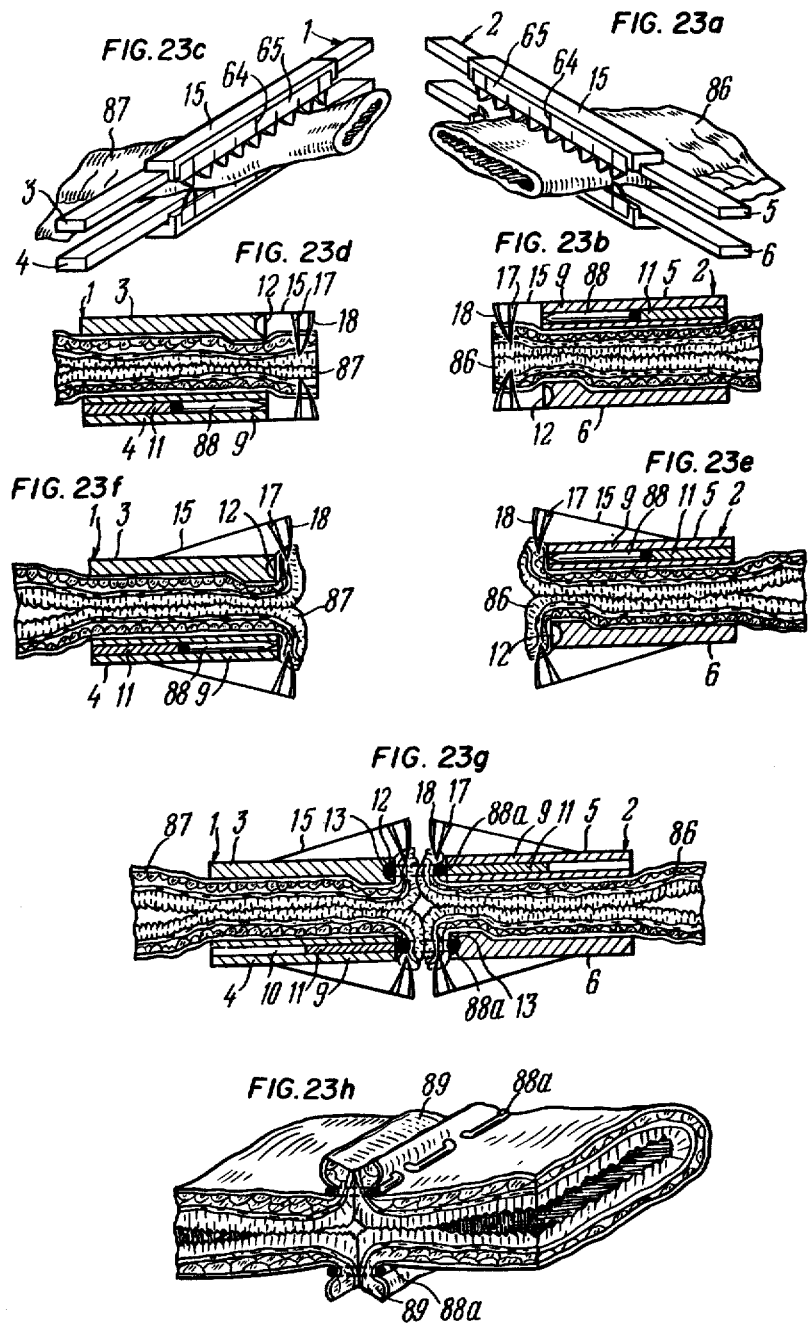

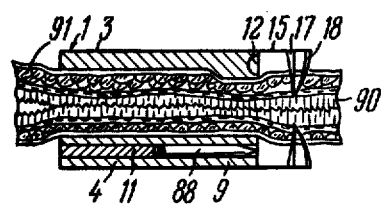
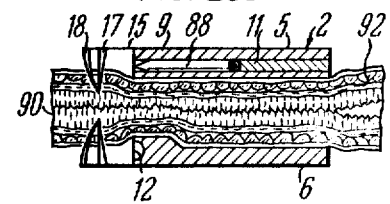
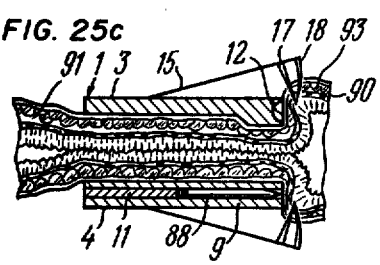
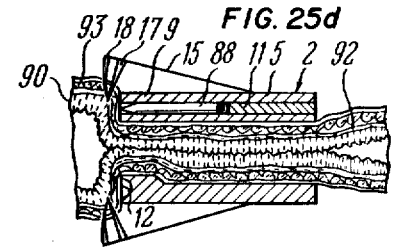
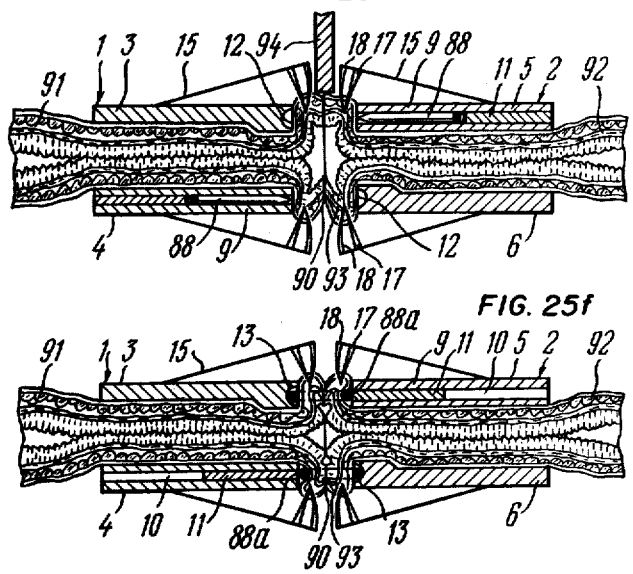
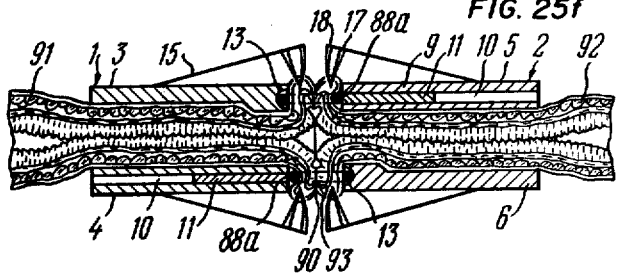
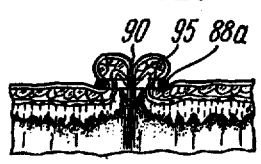
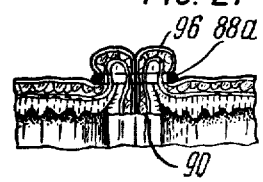

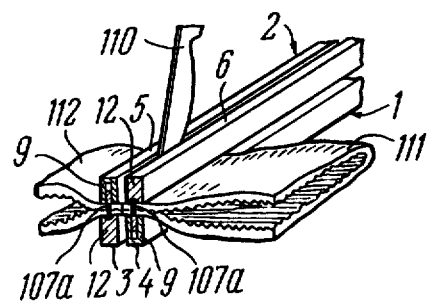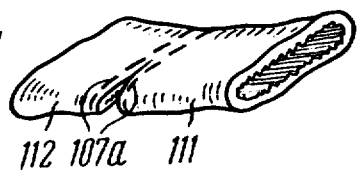
FIG.35  FIG.36
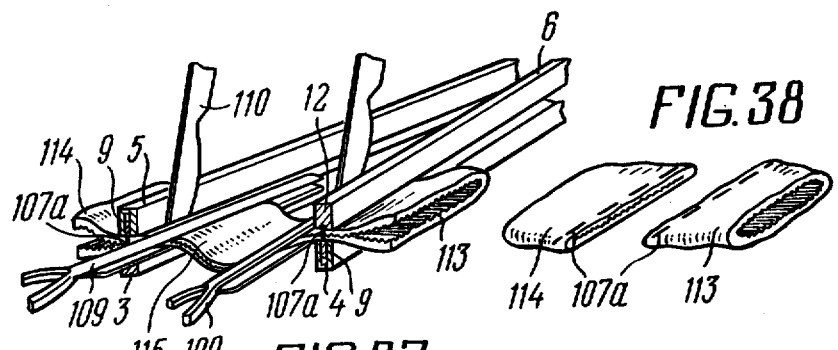
FIG.37  FIG.38
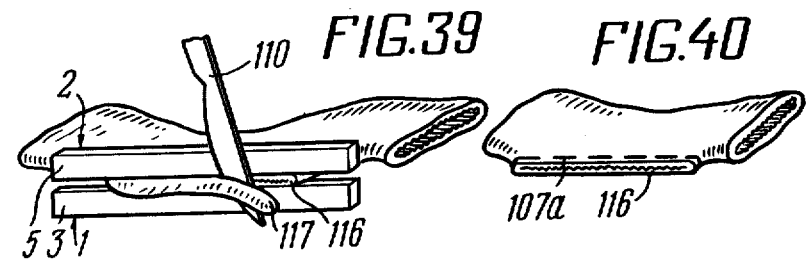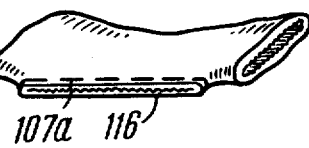
FIG.39  FIG.40

SURGICAL APPARATUS FOR SUTURING ORGANS WITH METAL STAPLES

BACKGROUND OF THE INVENTION

The present invention relates to medical equipment and more particularly to surgical apparatus for suturing organs, such as intestines, stomach, vessels or the like, with metal staples. The proposed apparatus is intended for suturing organs "end-to-end", "end-to-side" and "side-to-side" with the working parts of the apparatus disposed outside the organ being sutured.

The proposed apparatus may be used, specifically, for suturing the organs of the alimentary tract, for example, the intestines, with a one-tier or two-tier buried suture.

Known in the art is a surgical apparatus for suturing organs with metal staples "end-to-end", "end-to-side" and "side-to-side" with the working part of the apparatus disposed outside the organ being sutured (cf. U.S. Pat. No. 3,973,709). This prior art apparatus comprises two attachable clamps each having two jaws for clamping and fixing the organ being sutured. The clamps are detachably joined together so that the mating plane of the jaws of each clamp is perpendicular to the matingj plane of the clamps.

Mounted on the jaws of the clamps are dies with grooves for clinching staples, as well as magazines with slots for the staples and pushers. The magazines and dies interacting at the moment of suturing are situated on jaws of different clamps. The apparatus is furnished wih wedge drives for setting the pushers in motion.

Mounted also on the jaws of the clamps is a means for grasping and fixing the walls of the organ being sutured. It is made in the form of movable casings with toothed fixing members situated along the jaws at an equal pitch. On each of the jaws the casings are set in guides made as closed inclined slots worked in struts secured on the jaws, and cylindrical pins inserted into the slots and secured on the lateral ends of each casing. The guides provide for the limited movement of the casings in a plane perpendicular to the mating plane of the jaws and that of the clamps.

Every casing can take two extreme positions. In one, the forward position, corresponding to the moment of clamping and grasping the walls of the organ or organs being sutured, the tips of the teeth of the fixing members lie between the mating surfaces of the jaws of the clamps and at some distance in front of the mating surfaces of the clamps. In the other, extreme backward position, the tips of the teeth lie at some distance from the mating surfaces of the jaws of the clamps and approximately in the plane of the mating surfaces of the clamps. The tips of the teeth of the apparatus known in the art set only for one, constant suturing clearance between the interacting magazines and dies of the opposite clamps.

The prior art apparatus comprises a lock locking the movable casings in the forward position made in the form of a strip with stops pressing a casing to the trasversal wall of the closed guides. The casing is released from the locked position by disengaging the stops from the casing.

Cam lobes on each casing of the clamp serve for setting the movable casings in the backward position and interact with the corresponding cam lobes situated or the casings of the opposite clamp.

By means of cam lobes, the movable casings can be set in the backward position only after the clamps are joined and locked in position with a definite constant clearance between them. If this clearance is increased or the clamps are uncoupled the movable casings are shifted in the forward position and the toothed members fixing the walls of the organs get within the zone between the juxtaposed magazines and dies.

The clamps of the prior art apparatus are connected one with the other by means of a detachable joint at one end and rotatable hooks at the other. The rotatable hooks can fix the clamps at the moment of suturing only at one constant clearance in the mating plane between them.

The toothed elements fixing the walls of the organ in the prior art apparatus may have a variation of embodiments. An embodiment thereof comprises toothed elements in the form of needle-like teeth straight and bent in the longitudinal direction. The fixing teeth are disposed on strips set in movable casings along the jaws of the clamps. The strips with direct teeth are fixedly secured in the casings, while the strips with the bent teeth are movable in the longitudinal direction. As the movable strips move relative to the immobile ones the walls of the organ is grasped between the jaws of the clamp, by the paired fixing teeth. The movement of the strips with the bent teeth is carried out, by means of guides connected therewith, secured on the strips of the locks locking the movable bodies in the forward position.

The jaws of each clamp are hinged together.

For joining the jaws when compressing an organ to be sutured, each clamp comprises a figured spring plate, fastened with one end in one of the clamp jaws, and stepped recesses situated on the other jaw and interacting with the other end of the spring by one of its recesses depending on the thickness of the walls of the organ being clamped.

Scales on the clamp jaws serve for the mutual juxtaposition of the organ or organs being sutured in a direction longitudinal relative to the jaws.

The operation of the prior art apparatus is of the same type both when suturing organs "end-to-end" and when suturing them "end-to-side" and "side-to-side".

Before using the apparatus the clamps are parted. The strips of the locks of the movable casings, hooks and the drives of the pushers are set in the initial position.

One of the portions to be sutured is compressed between the jaws of one clamp within the scale for mutual juxtaposition of the organs to be sutured. When the organ is clamped the spring plate closes the jaws of the clamp.

Then the walls of the compressed organ are grasped and secured by means of the fixing members. For this the locking strips of the movable casings, are moved into the forward position. The guides secured on said strips shift the strips with the bent teeth which pierce the walls of the organ as their tips join the paired straight teeth. As the walls are being grasped the casings locked in the forward position are released.

In accordance with the position of the first area to be sutured relative to the scales of the first clamp, so the second area to be sutured is mounted and clamped according to the scales of the second clamp. Then the walls of the organ are secured and the movable casings are released from their locks as was done when handling the first clamp.

After dissecting the part of the organ to be removed along the frontal surface of the casings the clamps are joined. For this the axle and aperture of the detachable joint are superposed, the jaws of the clamps are approximated and the hooks are turned completely, rigidly connecting the clamps. A definite constant suturing clearance is thereby set between the jaws, and, consequently, between the conjugated magazines and dies. During the connection of the clamps the cam lobes of the movable casings of the means for grasping and fixing the walls of the organs to be sutured press against each other and withdraw the casings into the backward position only after the full turn of the hooks, placing the fixed edges of the walls into the suturing position.

By moving the wedge drives of the pushers, the staples are forced out of the magazine slots and the walls of the organ are sutured with an everted suture. Then the strips of the locks of the movable bodies are drawn backwards, due to the paired straight and bent fixing teeth which are drawn apart releasing the walls of the fixed organ.

Then the hooks are set in the initial position. The clamp jaws are drawn apart for which the stepped recesses of the spring are disengaged. Following that the apparatus is withdrawn from the surgical wound.

After applying the first tier of sutures with the aid of the prior art apparatus, the second tier of buried (invaginating) serous-muscular sutures are manually applied when suturing an organ or organs of the alimentary tract. A majority of surgeons regard the application of the second tier of buried sutures to be worthwhile.

The second tier of sutures is applied manually in individual interrupted buried sutures, one by one, first on the anterior wall of the sutured organ. The sutured organ is turned out in such a manner that the posterior wall of the organ faces the opening into the surgical wound. Then, the buried sutures are applied one by one to the posterior wall and the organs sutured with a two-tier buried suture are turned into the normal position.

The design of the prior art surgical apparatus does not provide for the synchronous movement of the interacting opposite casings of the means for grasping and fixing the walls of the organ to be sutured from the forward into the backward positions when joining and locking the clamps. Such movement takes place with some lagging behind of one casing in relation to the other, owing to the unequal friction in the guides of the casings of the opposite clamp jaws, errors in the shape and mutual situation of the cams, acting upon each other when the clamps are joined, and also the possibility of unequal preliminary shift of the casings towards the jaws after the walls of the organs are secured and the part to be removed is cut off along the jaws of the separate clamps. As a result of this, the edges of the walls being juxtaposed for suturing, protrude beyond the fixing members of the casings of one clamp, are set in the position of suturing earlier than the edges of the walls, projecting beyond the fixing members of the opposite casing of the other clamp.

Owing to this the distance from the resection line of the sutured edges of the walls to the suture is unequal before suturing and, consequently, the juxtaposition of the edges of the walls of the sutured organ is not accurate enough.

Nor does the design of the prior art apparatus provide for suturing organs with different clearances between the magazines and the dies, that is, for adjusting the clearance of the deformed staples according to the thickness of the walls being sutured. The setting of the movable casings of the means for grasping and fixing the walls of the organ to be sutured from the forward into the backward position takes place in the prior art apparatus only upon the complete rotation of the hooks, securing a quite definite, single clearance between the joined clamps. Only given this clearance the fixing members can be set in the position enabling the suturing of the walls of the organ or organs. At an increase of the clearance the movable are shifted towards the forward position, while the fixing members get into the zone between the interacting magazines and dies.

The design of the prior art apparatus does not provide for suturing the walls of organs end-to-end with contact of the walls along the surface of the cut and suturing with a suture inverted relative to the cavity of the organ with contact between the external surfaces of the walls of the organ, as used in surgical practice.

Nor does the design of the prior art apparatus allow its use for applying a second tier of buried staple sutures, used for suturing the organs of the alimentary tract. The means for grasping and fixing the walls of the organs, whose casings are situated in the backward position only after joining and securing the clamps at a constant clearance, does not provide for burying the edges of the fixed walls of the organs or the first tier of sutures, or for placing the walls of the organs above it into the suturing position in order to apply a second tier of sutures.

It should also be borne in mind that the design of the prior art apparatus does not provide for the adjustment of the suturing clearances. This is essential when placing the second tier of sutures with the use of an apparatus for placing the first tier of sutures, since the thickness of the walls being juxtaposed for suturing through the serous-muscular layers when placing the second tier of sutures differs substantially from the thickness of the edges of the walls set between the magazines and the dies when the first tier of sutures is being placed.

Another disadvantage of the prior art apparatus is the necessity of placing the second tier of buried sutures by hand, by creating a sequence of individual interrupted sutures. This is labor-consuming and takes considerable time.

Due to the fact that the casings for grasping and fixing the walls of the organ are set in the backward position only after the clamps are joined, the prior art apparatus does not provide for suturing organs during resections aimed at the complete closure of the lumen of organs.

SUMMARY OF THE INVENTION

It is an object of the present invention to provide a surgical apparatus for suturing organs with metal staples "end-to-end", "end-to-side" and "side-to-side" with the working part of the apparatus disposed outside the organ being sutured, allowing to raise the precision of the reciprocal situation of the sections of the opposite walls of the organ being sutured in regard to the suturing line and thereby improve the conditions for the regeneration of tissues.

Another object of the invention is to provide the possibility for creating the optimal degree of compressing the tissues in suture when the thickness of the walls of the organ varies over a wide range.

Still another object of the invention is to considerably expand the functional applications of the apparatus by providing the possibility of applying sutures not only everted relative to the cavity of the organ, but for suturing the walls of organs end-to-end with the walls being in contact along the surface of the section, for suturing with a suture inverted relative to the cavity of the organ, for suturing walls with a two-tier buried suture, used in surgical practice for the application of anastomoses, and also to provide the possibility of suturing organs by various method used in surgical practice when resecting organs.

Yet another object of the invention is to simplify the handling of the apparatus and raising the reliability of its operation.

The invention essentially resides in a surgical apparatus for suturing organs with metal staples "end-to-end", "end-to-side" and "side-to-side" with the working part of the apparatus disposed outside the organ being sutured, comprising two clamps having two jaws for clamping and fixing the organ being sutured and detachably joined together so that the mating plane of the jaws of each clamp is perpendicular to the mating plane of the clamps. Magazines with slots for staples are mounted in the jaws, and staple pushers, dies with grooves for clinching the staples, are also provided in the device. The magazines and dies which interact at the moment of suturing are situated on the jaws of different clamps. Means mounted on the jaws of the clamps, provide for grasping and fixing the walls of the organ to be sutured, embodied as casings with members fixing the walls of the organs, are situated along the jaws with said casings disposed in each of the jaws in guides providing for the restricted movement of the casings in a plane perpendicular to the mating plane of the jaws and the mating plane of the clamps so that each of said casings may be in two extreme positions. In one position, the forward, the fixing members lie between the mating surfaces of the clamps and at some distance in front of the mating surfaces of the clamps, and in the other extreme position, the backward, the fixing members lie at some distance from the mating surfaces of the clamp jaws and approximately in the mating surfaces of the clamp jaws and approximately in the mating planes of the clamps. Locks are provided and mounted in the jaws for locking the movable casings in the forward position, with the jaws of the clamps provided with locks for locking the movable casings in the backward position and retaining the casings regardless of the interrelated positions of the clamps and the width of the suturing clearance between the magazines and the dies.

Compared to the apparatus known in the art, the proposed surgical apparatus is capable of applying sutures of a higher quality and has much wider functional applications. Also, in distinction from the known apparatus: the apparatus of the invention provides for the adjustment of the suturing clearances according to the thickness of the walls of the organ; provides for suturing the walls of the organ end-to-end with contact between the walls along the surface of the section; provides for suturing the walls of the organ with a suture inverted relative to the cavity of the organ; provides for placing two-tier buried sutures; and provides for the suturing of the lumen of organs with application of sutures both on the remaining and on the portion of the organ being removed, as well as for the suturing of a lateral portion of organs and, besides, provides for the operation of the apparatus deep within the surgical wound.

The clamp jaws are provided with locks locking the movable casings in the backward position, so as to allow retaining the walls of the organs both with the clamps being separated and joined, and said clamp jaws preclude the fixing members and movable casings from getting into the zone between the interacting magazines and the dies of the opposite clamps regardless of the clearance between them in the joined position, and they also allow retaining the walls of the organs when the jaws of each of the clamps are parted, separately or together.

Due to the novel and distinctive features of the apparatus, its functional range has been considerably increased, with an extension of its practical applications, so that the apparatus can be used for applying anastomoses at different levels of the alimentary tract, with large differences in the thickness of the walls of the organs, such as, for example, when suturing the stomach with an intestine, and in other areas where a wide diversity of variants in the juxtaposition of the walls of the organs being sutured that they have all found practical application, and also the device is applicable for the resection of organs.

In an apparatus, in which the guides of the casings are closed slots made on the jaws of the clamps with inclined portions, movable in which are cylindrical pins secured on the casings, it is desirable that the locks for locking the movable casings in the backward position be spring-loaded cantilever plates secured on the jaws of the clamps, their free ends interacting with shoulders made on the movable casings, which ensures reliable fixation of the movable casings in the backward position.

The free ends of the spring-loaded plates may be inclined to the mating plane of the jaws of the clamps and the shoulders may be formed by the wall of the open slots in the body of the movable casings, and the locks locking the movable casings in the forward and backward positions may be secured on common strips movably set along each jaw of the clamps and occupying one of two extreme positions. In one of the extreme positions, movable casings are locked in the forward position and in the other extreme position, the movable casings are locked in the backward position, and the length of the working portion of each of the spring-loaded plates, interacting with the open slots, is shorter than the run of the movable strips.

This provides for convenience and the automatic locking of the movable casings in the backward position, and for the convenience in releasing the casings locked in the backward position for setting them in the forward position, and also when releasing the casings locked in the forward position.

It is desirable that the jaws of each clamp be connected with the jaws of the other clamp through a means for altering the distance between the mating surfaces of the clamps.

In an embodiment of the apparatus with the locks of the movable casings in the backward position combined with a means for changing the distance between the mating surfaces of the clamps, and linking the jaws of one clamp with those of the other, it is possible to adjust the degree of compression of the tissues in the suture.

The provision of locks locking the movable casings in the backward position prevents the members fixing the walls of the organs from getting into the zone between the magazines and the dies when the suturing clearance is increased with the aid of the means for altering the distance between the mating surfaces of the clams, whereas the utilization of said means in an embodiment of the apparatus without the locks of the movable casings in the backward position is pointless.

The provision for adjusting the suturing clearance assumes great importance in an apparatus embodied according to the invention, which allows one to suture organs with different juxtaposition of walls when applying both single-tier and two-tier sutures to different organs, and when the thickness of the tissues compressed between the magazines and the dies of the clamps may vary in a wide range.

It is desirable that at one of their ends the clamps be connected through a detachable joint, and that the means for altering the distance between the mating surfaces of the clamps be made in the form of a rotatable cam fixed on one of the clamps. The cam's working surface having the configuration of a portion of a diverging spiral with an angle of helix not greater than the angle of self-breaking, and said cam interacting with a pin fastened on the other clamp.

Such a design of the means for altering the distance between the mating surfaces of the clamps provides a reliable mutual fixation of the interacting magazines and dies in the process of suturing with different clearances between them, and also provides for convenience in joining the clamps and adjusting the suturing clearances.

It is advisable to secure the rotatable cam on the jaws of one of the clamps, between the detachable joint and the means for grasping and fixing the walls of the organs being sutured, mounted at the ends of the clamp jaws. This ensures the possibility for controlling the apparatus only from the direction of the entrance into the surgical wound, which enables use of the apparatus not only in cases when the organs to be sutured can be brought out onto the surface of the surgical wound, for example, when suturing the small intestine, but also when working in the depth of the surgical wound, when the organs being suturated cannot be brought out onto the surface, for example, in resection of the stomach with the application of gastrointestinal anastomoses.

It is advisable to furnish the apparatus with a device for burying the first tier of sutures, connecting organs when a second tier of sutures is being placed, made in the form of a fork intended for encompassing the sutured organs along the first tier of sutures and disposing said fork at the moment of placing the second tier of sutures together with the sutured organs encompassed thereby between the jaws of the clamps, so that its longitudinal axis is approximately parallel to the longitudinal axis of the apparatus, and the length of the prongs of the fork correspond to the length of the magazine and die.

The placing of the second tier of sutures with the utilization of the device for burying the first tier which is difficult for access, is possible due to the embodiment of the clamps of the apparatus with locks locking the movable casings in the backward position ensuring the possibility, following the grasping and fixation of the walls of the organs to be sutured laterally to the first tier of sutures, of parting and securing the fixing members in the backward position when drawing apart the clamp jaws for burying the first tier of sutures and juxtaposing above them the fixed walls for placing the second tier of sutures, and setting the suturing clearance between the magazines and dies according to the thickness of the walls of the organs being sutured.

The jaws of the fork may be round or circular and U-shaped in cross-section and their channels may be facing one another. This provides for accuracy and convenience in setting the prongs of the fork along the first tier of sutures depending on the type of suture: either inverted relative to the lumen of the organs, or everted, which is achieved in that the shape of the prongs of the fork on the side facing each other corresponds to the type of suture.

For burying an inverted suture it is advisable that the jaws of the fork have a circular shape in cross-section on the sides facing each other, the greatest convenience and precision of burying an everted suture are provided with a U-shaped cross-section of the jaws with the channels facing each other.

It is advisable that the jaws of the fork be resilient and that they be furnished with a detachable locking member preventing the divergence of their tips at the moment when the first tier of sutures is being buried and the second tier of sutures placed. This will provide for atraumatic compression of the sutured walls when their thickness changes in a wide range and the reliable burying of the first tier of sutures.

It is desirable that recesses be made on the tips of the prongs of the fork for fastening the locking member so as to exclude accidental unlocking of the locking member, and secure the atraumatic withdrawal of the fork from the surgical wound after the placement of the second tier of sutures.

The locking member may be embodied in the shape of a frame with a rectangular window. This will provide for the rapid and convenient connection of the prongs of the fork, as well as their disconnection following the placement of the second tier of sutures.

BRIEF DESCRIPTION OF THE DRAWINGS

The invention will now be described with reference to preferred embodiments thereof taken in conjunction with the accompanying drawings, wherein:

FIG. 5a, b and c show the reciprocal disposition of the locks of one of the casings of the means for grasping and fixing the walls of the organs being sutured, and of a casing and fixing teeth with a lock strip in the extreme backward position;

FIG. 6a, b, and c show the reciprocal disposition of the locks of one of the casings of the means for grasping and fixing the walls of the organs being sutured, and of a casing and fixing teeth with a lock strip in the extreme forward position;

FIG. 7a, b, and c show the mutual disposition of the locks of one of the casings of the means for grasping and fixing the walls of the organs being sutured, and of a casing and fixing teeth with a lock strip in the extreme forward position and a casing in the backward position;

FIG. 8a, b and c show the mutual disposition of the locks of one of the casings of the means for grasping and fixing the walls of the organs being sutured, and of a casing and fixing jaws with a lock strip in the intermediate position;

FIG. 9 is an enlarged elevational view of the means for altering the distance between the mating surfaces of the clamps of the apparatus; according to the invention, on an enlarged scale;

FIG. 10 is a longitudinal sectional view taken along the line X—X of FIG. 3;

FIG. 11 is a sectional view taken along the line XI—XI of FIG. 10;

FIG. 12 is a sectional view taken along the line XII—XII of FIG. 10;

FIG. 13 is another elevational view showing a surgical apparatus for suturing organs with metal staples made in accordance with the invention, and with a device for burying the first tier of sutures;

FIG. 14 is a longitudinal sectional view taken of the apparatus of FIG. 13;

FIG. 15 shows the fork of the device for burying the first tier of sutures, according to the invention;

FIG. 16 is a sectional view taken along the line XVI—XVI of FIG. 13;

FIG. 17 is a cross-section of the jaws of the fork of round shape, applied to organs sutured with an inverted suture;

FIG. 18 shows a U-shaped cross-section of the jaws of the fork applied to organs sutured with an everted suture;

FIG. 19 is a cross-sectional view taken along the line XIX—XIX of FIG. 13;

FIG. 20 is a sectional view of the end of the fork and the pin to which it is attached, as shown in FIG. 13;

FIG. 21 shows a yoke for burying the first tier of sutures, applied to an organ, according to the invention;

FIG. 22 represents another fragmentary view of part of the apparatus with the yoke for burying the first tier of sutures in the process of applying the second tier of sutures;

FIGS. 23a, b, c, d, e, f and g are schematic representations of the main stages in suturing organs with an everted suture by means of the apparatus of the invention;

FIG. 24 is another perspective view in cross-section of organs, sutured with an everted suture by means of the apparatus of the invention;

FIGS. 25a, b, c, d, e and f are schematic representations of the main stages in suturing with the aid of the apparatus, according to the invention, of the walls of organs end-to-end with wall contact along the surface of the section;

FIG. 26 is a cross-section of a suture with juxtaposition of the walls of organs end-to-end, applied by means of the apparatus, according to the invention;

FIG. 27 is a cross-section of an inverted suture, applied by means of the apparatus, according to the invention;

FIG. 35 is a fragmentary, perspective view in cross-section of the clamps of the apparatus, at the moment of applying sutures to portions of organs both remaining and being removed, with the dissection of the walls of the organs between the rows of sutures;

FIG. 36 is a fragmentary, perspective view showing an organ with sutures applied with the aid of the apparatus to a remaining portion and a portion being removed with the partial dissection of the organ between the sutures;

FIG. 37 is a fragmentary, perspective view, partially in section, of the clamps of the apparatus at the moment of applying sutures of two remaining ends of an organ, situated at some distance one from another during the partial resection of an organ;

FIG. 38 is a fragmentary, perspective view showing an organ with sutures applied with the aid of the apparatus to two remaining ends following the partial resection of an organ;

FIG. 39 is a fragmentary, perspective view of one pair of jaws of the clamps of the apparatus, at the moment of suturing a lateral portion of an organ and dissecting a portion to be removed; and FIG. 40 is a fragmentary, perspective view showing the lateral portion of an organ, sutured with the aid of the apparatus of the invention.

DESCRIPTION OF THE PREFERRED EMBODIMENTS

Figure 1:
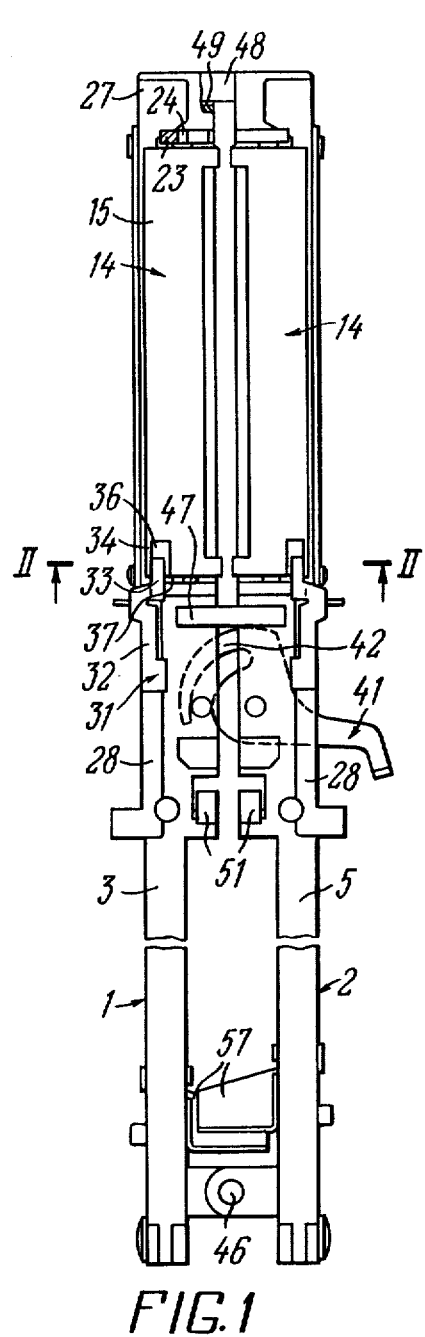
FIG. 1 is a top or front elevational view showing a surgical apparatus for suturing organs with metal staples, made in accordance with the invention.

A surgical apparatus for suturing organs with metal staples comprises two clamps 1 and 2 (FIG. 1), detachably joined together. The clamp 1 has jaws 3 and 4 (FIG. 2), and the clamp 2—jaws 5 and 6 disposed in the joined clamps in pairs, one jaw opposite the other: the jaw 3 of the clamp 1 opposite the jaw 5 of the clamp 2, and the jaw 4—opposite the jaw 6.

The mating plane I—I of the jaws 3 and 4 and of 5 and 6 of each jaw 1 and 2 is perpendicular to the mating plane II—II of the clamps 1 and 2.

There is a clearance between the mating surfaces 7 of the jaws 3, 4, 5 and 6 of each clamp 1 and 2, corresponding to the thicknesses of the tissues being clamped, the clamps 1 and 2 are also connected with a clearance between the mating surfaces 8, which is adjusted according to the thickness of the walls being sutured.

Mounted on the jaws 4 and 5 of the clamps 1 and 2 are removable magazines 9 with slots 10 for the staples and staple pushers 11, while mounted on the jaws 3 and 6 are dies 12 with grooves 13 for clinching the staples. The magazines 9 and the dies 12, interacting at the moment of suturing, are situated on the jaws 3 and 5, 4 and 6 of the different clamps 1 and 2.

The apparatus comprises also a means 14 (FIGS. 1 and 2) for grasping and fixing the walls of the organs being sutured. It is made in the form of casings 15 (FIG. 2) with locking members 16, disposed along the jaws 5 and 6 (FIG. 3) of the clamp 2 and similarly along the jaws 3 and 4 (not shown in FIG. 3) of the clamp 1. The embodiment and operating principle of the members fixing the walls of the organs may vary. One embodiment of the apparatus, according to the invention, as represented in the drawings, has the locking elements made in the form of interacting straight 17 and bent 18 teeth, the straight teeth 17 are siutated on the strips 19 (FIG. 2), while the bent teeth 18 are situated on the strips 20 over a uniform pitch. The strips 19 are fixedly built into the casings 15, while the strips 20 with the bent teeth 18 are movable relative to the casings 15 in the longitudinal direction. The strips 19 and 20 are secured in the casings 15 so that they can easily be removed therefrom.

Figure 4:
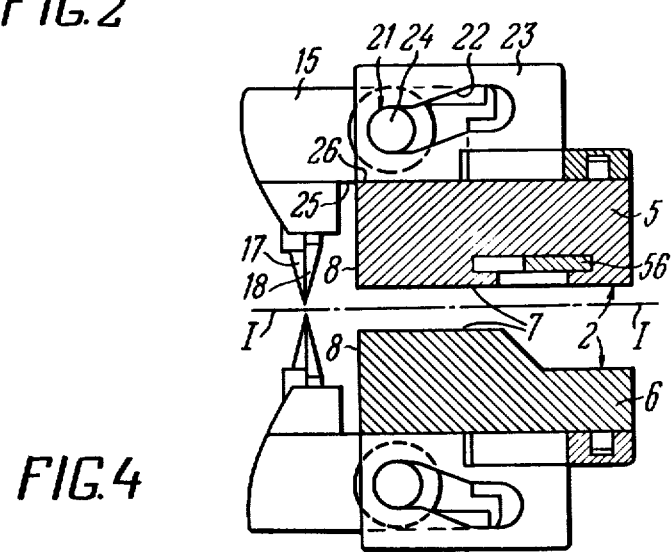
FIG. 4 is an enlarged cross-sectional view taken along the line IV—IV of FIG. 3.

In another embodiment (not shown in the drawings), used for surgical apparatus and instruments, the locking elements or members may be made in the form of perforated teeth longitudinally disposed in the casings 15 perforated teeth, into which an elongated needle for piercing the walls of the organs is inserted. The casings 15 are mounted on each of the jaws 3, 4, 5 and 6 in guides 21 (FIG. 4), providing limited movement of each of said casings 15 in a plane perpendicular to the mating plane I—I of the jaws 3, 4, 5 and 6 of the clamps 1 and 2 and of the mating plane II—II (FIG. 2) of the clamps 1 and 2, so that each of the casings 15 may occupy one of two extreme positions. In one of them, the forward extreme position, showed in FIG. 4 and corresponding to the moment of clamping and grasping the walls of the organs being sutured, with clamps apart, the tips of the fixing teeth 17 and 18 lie between the mating surfaces 7 of the jaws 5 and 6 (or 3 and 4, not shown in FIG. 4) and at some distance in front of the mating surfaces 8 of the clamps. In the other position, the backward extreme position of the casings 15, shown in FIG. 2, the tips of the fixing teeth 17 and 18 lie at some distance from the mating surfaces 7 of the jaws 3, 4, 5 and 6 of the clamps 1 and 2, respectively, and approximately within the mating planes 8 of the clamps 1 and 2.

In a variant of the embodiment of the apparatus represented in the drawings, the guides 21 (FIG. 4) are made in the form of closed through slots with inclined portions 22, made in the struts 23, and with cylindrical pins 24, inserted in the slots and fastened on the lateral butts of the casing 15. The struts 23 (FIG. 3) are disposed on two sides relative to the casing 15 and are rigidly fastened on the jaws of the clamp.

The apparatus of the invention does not rule out still another embodiment of the guides, providing, for example, for the sliding movement of the casings 15 from the forward to the backward position (not shown).

A casing 15 (FIG. 4) is provided with a bearing surface 25, interacting with the surface 26 of the jaw, on which it is fastened, and serving as a rest during the movement of the casings 15 from one extreme position to another.

Each of the jaws of the clamps comprises a lock 27 (FIG. 5a) for locking the movable casing 15 in the forward position. It is made in the form of a movable strip 28 with a rest 29 secured along a jaw, for example, the jaw 5, and the rest 29 interacting with the lug 30 of casing 15, fastened on this jaw.

Each of the clamp jaws comprises also a lock 31, for locking the movable casing 15 in the backward position. In this position, the lock 31 retains the movable casing 15, whether the clamps are separated or joined and whatever the suturing clearance is between the interacting magazines 9 (FIG. 2) and dies 12.

The provision of the locks 31 locking the movable casings 15 in the backward position expands the functional application of the apparatus. The possibility of locking the movable casings 15 in the backward position allows one to draw apart the walls of the organs, and fixed and secure them in the backward position with the clamps 1 and 2 parted. As a result of this, the edges of the walls fixed in the process of joining the clamps 1 and 2 move towards each other and ensure the uniform juxtaposition of the walls to be sutured.

The locking of the casings 15 in the backward position by means of the locks 31 makes it convenient to observe the internal surface of the walls of the organs with the jaws 3, 4, 5, and 6 of the clamps 1 and 2 separated, when it is necessary to inspect the cavities of the organs in the process of the operation. The separated edges of the walls will not obstruct observation.

The lock 31 locking the casings 15 in the backward position provides also for the possibility of changing the suturing clearance according to the thickness of the walls to be sutured, since, regardless of the distance between the jaws 3, 4, 5 and 6 of the clamps 1 and 2, the members 16 fixing the walls of the organs do not get into the suturing zone between the magazines 9 and the dies 12.

The locks 31 of the movable casings 15 make it also possible to use the apparatus, for implementing newly proposed techniques for suturing the walls of organs end-to-end with contact of the walls along the surface of the section, for suturing walls with an inverted suture, and for placing two-tier buried sutures when suturing organs of the alimentary tract. With all the aforementioned methods, the lock 31 provides for retaining the casings 15 in the backward position and securing the fixed walls of the organs in the position for suturing.

Locking the movable casings 15 in the backward position by means of the locks 31 ensures also the possibility of using the apparatus, not only for making anastomoses, but also for suturing organs with the purpose of closing a lumen completely.

Figure 3:
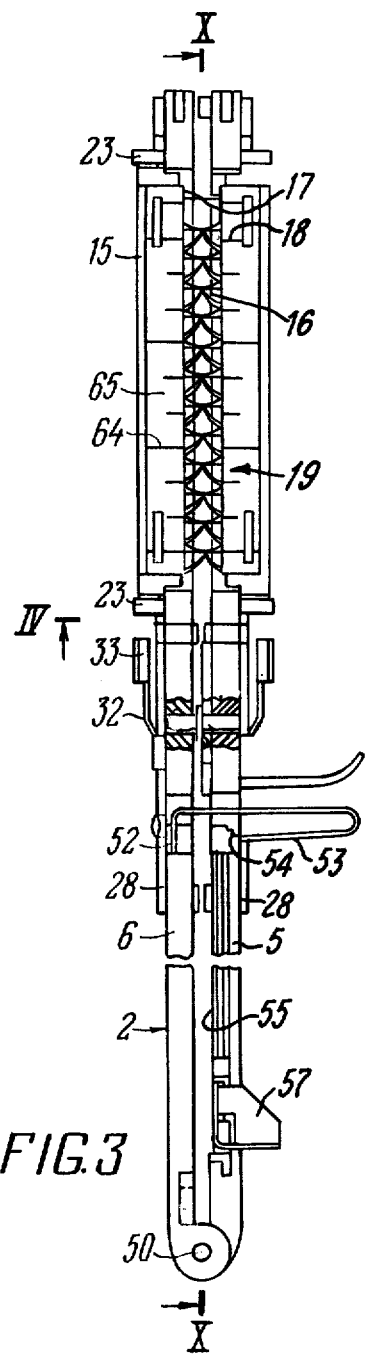
FIG. 3 is a side elevational view showing one of the clamps of the apparatus when locking the casings of the means for grasping and fixing the walls of the organs to be sutured in the forward position.
Figure 2:
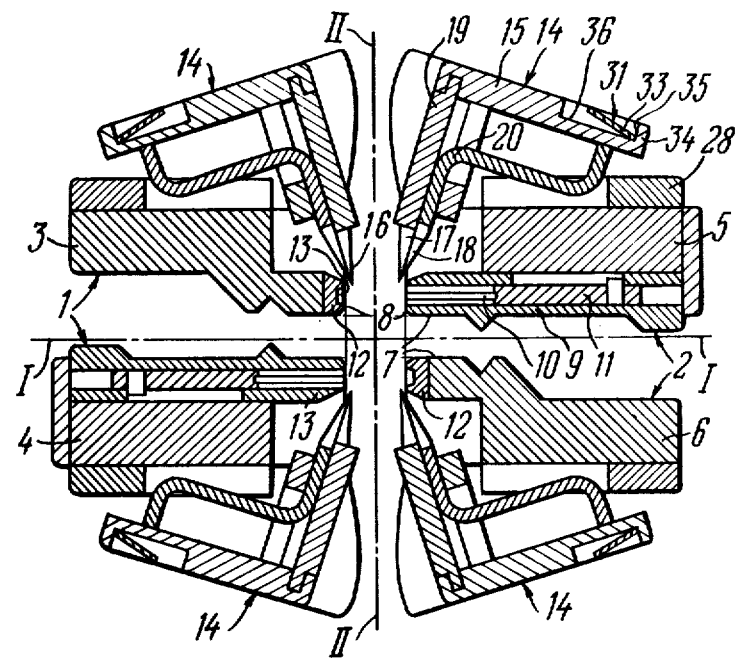
FIG. 2 is an enlarged cross-sectional view taken along the lines II—II of FIG. 1.

The lock 31 locking the movable casings 15 in the backward position, when using the variant of the embodiment of the guides 21 (FIG. 4) which form closed slots with inclined portions 22 and in which are cylindrical pins 24 secured on the casings 15, appear as spring-loaded cantilever plates 32 (FIGS. 1 and 3). The free ends 33 of the spring-loaded plates 32 interact with the shoulders 34 (FIG. 2) made in the movable casings 15. The free ends 33 are inclined to the mating plane I—I of the jaws 3, 4, and 5, 6 of the clamps 1 and 2. This allows, when encountering the casing 15 as the latter slides from the forward into the backward position, to raise automatically the free end 33 of the spring-loaded plate 32, which then slips behind the shoulder 34, retaining the casing 15 in the backward position.

The shoulders 34 are formed by the wall 35 of the open slots 36 in the body of the movable casings 15, open from the direction of the butt 37 (FIG. 1) of the casing 15, while the spring-loaded plates 32 of the locks 31 are secured in the strips 28 of the locks 27 of the movable casings 15 in the forward position. The strips 28 are disposed movably along each jaw of the clamps 1 and 2 and occupy one of two extreme positions. In one extreme position of the strips 28, as shown in FIG. 5a, the movable casings 15 are locked in the forward position. In the other extreme position best shown in FIG. 1, the movable casings 15 are locked in the backward position, the length of the working portion of the free ends 33 of the spring-loaded plates 32, interacting with wall 35 (FIG. 2) of the open slots 36, is shorter than the run of the movable strips 28. This provides for the automatic withdrawal of the spring-loaded plates 32 (FIG. 1) from the slots 36 when the strip 28 of the locks 31 is moved towards its initial position.

Each strip 28 comprises also a guide 38 (FIG. 5a), intended for shifting the movable toothed strip 20. The strip 20 has a bent portion 39 with an L-shaped slot 40, for accommodating the guide 38.

The locks 27 and 31 of the movable casings 15 of each jaw of the clamps, for example, the jaw 5, the movable casing 15 and the teeth 17 and 18 (FIG. 5b) fixing the walls of the organs, may occupy four typical interrelated positions during the performance of the apparatus:

Position 1 (FIGS. 5a, b, c). When the strip 28 (FIG. 5a), which is the drive of the locks 27 and 31 that lock the movable casings 15 in the forward and backward positions, and also the drive of the toothed strip 20, is in the extreme backward position, the free end 33 of the spring-loaded plate 32 is withdrawn from the slot 36 of the casing 15. The rests 29 are engaged with the lugs 30 of the casing 15, fixing it immovably relative to the jaw 5 in the forward position. The strip 20 with the bent teeth 18 (FIGS. 5b, c) is in the initial position and the paired straight 17 and bent 18 teeth, interacting when grasping the tissue, are parted.

Position 2 (FIGS. 6a, b, c). The strips 28 (FIG. 6a) are in the extreme forward position. The rests 29 are disengaged from the lugs 30 of the casing 15, thus unlocking it. The free end 33 of the spring-loaded plate 32 is situated opposite slot 36 (FIGS. 6a, b) of the casing 15 in a direction crosswise to the jaw 5. The strip 20 with the bent teeth 18 (FIG. 6c) is situated in the extreme forward position, with the paired fixing teeth 17 and 18 closed, grasping the walls of the organ, provided they are clamped between the jaws of the clamp.

Position 3 (FIGS. 7a, b, c). The strip 28 (FIG. 7a) and, consequently, the rests 29 and toothed strip 20 are in the extreme forward position. The movable casing 15 (FIGS. 7a, b) is shifted into the backward position and locked by the free end 33 of the spring-loaded plate 32, set against the wall 35 of the slot 36 of the casing 15. The paired fixing teeth 17 and 18 (FIG. 7c) are joined and, provided they have grasped the walls of an organ between them, they retain them in the separated state with the casing 15 locked in the backward position regardless of the mutual disposition of the clamps 1 and 2 (FIG. 1) such as at different suturing clearances as well as in the case when the clamps 1 and 2 are separated. With the casing 15 in the backward position just examined and the paired fixing teeth 17 and 18 (FIG. 7c) joined, various manipulations are carried out with the fixed walls of the organs, depending on the method of using the apparatus, including suturing organs with variable clearances corresponding to the thickness of their walls.

Position 4 (FIGS. 8a, b, c). The strip 28 (FIG. 8a) is shifted towards the backward position by a length, exceeding that of the working part of the spring-loaded plate 32. The free end 33 of the plate 32 is disengaged from the wall 35 (FIGS. 8a, b) of the slot 36 in the casing 15, having unlocked its backward position. The toothed strip 20 is shifted backwards by the length of the pitch between the teeth so that the paired fixing teeth 17 and 18 (FIG. 8c) are separated. In this state, the walls of the organs are released from fixation following suturing.

The jaws 3 and 4 (FIG. 2) of the clamp 1 of the apparatus are connected with the jaws 5 and 6 of the clamp 2 by the means 41 (FIGS. 1 and 9) for altering the distance between the mating surfaces 8 (FIG. 2) of the clamps 1 and 2. Due to presence of the locks 31 locking the movable casings 15 in the backward position, preventing the fixing members 16 from getting into the zone of suturing between the magazines 9 and the dies 12 at any reciprocal position of the clamps 1 and 2, the means 41 (FIGS. 1 and 9) for altering the distance between the mating surfaces 8 (FIG. 2) of the clamps 1 and 2 provides for suturing organs with different clearances between the magazines 9 and dies 12 corresponding to the thickness of the walls of organs which, of course, are varying in a wide range. This increases the quality of the sutures applied with the aid of the apparatus by ensuring the uniform separation and juxtaposition of the organs being sutured, as well as the tightness of the suture and hemostasis of tissues with atraumatic compression of the tissues with metal staples, regardless of the thickness of the walls being sutured. This, in turn, greatly expands the range of the applications of the apparatus since it allows to suture not only of the same organs, for example, the intestine at different levels (a small intestine with a small one, a large intestine with a large one, a small intestine with a large intestine), but also allows suturing of different organs, such as the stomach with an intestine, the thickness of whose walls differs considerably from the thickness of the walls of the intestine.

The means 41 (FIG. 1) for altering the distance between the mating surfaces 8 (FIG. 2) of the clamps 1 and 2 may have different embodiments, with the use, for example, of screw pairs or wedge pairs, bringing the jaws of the clamps 1 and 2 (not shown) together or apart.

In the variant represented in the drawings, it is made in the form of a rotatable cam 42 (FIG. 9). The cam is fastened by means of an axle 43 on the jaws of one of the clamps, for example 2, and interacts with a pin 44, fastened on the jaws of the other clamp, for example 1. The working surface 45 of the cam 42 has the configuration of a portion of a diverging spiral with an angle of helix within the limits of the angles of self-braking, for example, up to 5°. One of the embodiments of the apparatus has the spiral's angle of helix of about 3.5°.

Securing the clamps 1 and 2 relative to one another is carried out, together with the cam 42, by a detachable joint 46 (FIG. 1), situated at the end of the clamps 1 and 2. The cam 42 is situated in the middle part of the apparatus between the means 14 for grasping and fixing the organs to be sutured and the joint 46.

Such a disposition of the cam 42 provides for conveniently handling the apparatus within a surgical wound, for example, when making gastrointestinal anastomoses, because manipulations for joining and parting the clamps 1 and 2 have to be carried out only from the direction of the cam 46, that is, from the entrance to the surgical wound.

Because the clamps 1 and 2 are hinged together, the clearance between the mating surface 8 (FIG. 2) of the clamps 1 and 2 changes wedgewise in the longitudinal direction of the apparatus and only in one position of the clamps 1 and 2 it can be uniform along the entire length of the magazines 9 and the dies 12. However, the magazines 9 and the dies 12 are situated on the ends of the jaws 3, 4, and 5, 6 of the clamps 1 and 2, opposite to the joint 46 (FIG. 1), while the length of the suture being applied is several times less than the length of the clamps 1 and 2, due to which the deviation from parallelism in the manual disposition of the magazines 9 (FIG. 2) and the dies 12 within the adjustable range of the suturing clearances is small and is of no practical importance.

For accurate juxtaposition of the mated jaws 3, 5 and 4, 6 (FIG. 2) of the clamps 1 and 2 in the process of suturing, a fork 47 is secured on each of the jaws 5 and 6 of the clamp 2 (FIG. 1), encompassing, when the clamps 1 and 2 are being joined, the corresponding jaw 3 or 4 of the clamp 1, as shown in FIG. 1 for the jaws 3 and 5, and the lug 48, entering the slot 49 of the jaw 3. A similar lug and slot are made in the jaws 6 and 4 correspondingly, not shown in FIG. 1.

The jaws 3, 4, and 5, 6 (FIG. 2) of each clamp 1 and 2 are linked by means of a joint 50 (FIG. 3). For joining the jaws, for example 5 and 6 of the clamp 2, when compressing organs and grasping the walls thereof with the fixing members 16, each clamp is provided with a resilient lock 51. It is made in the form of a bent plate, one of its ends 52 being fastened on one of the jaws of the clamp, for example, the jaw 6 of the clamp 2, and its free end 52 being connected with the stepped recesses 54 of the other jaw, for example, the jaw 5.

Drives 55 (FIG. 10) of the pushers 11 are movably secured on the jaws 4 and 5 (FIG. 2) of the clamps 1 and 2 containing the magazines 9. The drive 55 is made with a wedge 56 at one end and a handle 57 on the other. The wedge 56 is disposed in the slot 58 on the jaw, for example, the jaw 5 of the clamp 1, of which the through hole 59 in the magazine 9 serves as a continuation thereof. During the movement of the drive 55, the wedge 56 enters the longitudinal hole 59 of the magazine 9 and crosswisely actuates the pushers 11 situated in the slots 10 of the magazine 9. As the pushers 11 move, the staples (not shown in FIG. 10) are pushed out of the magazine 9, provided the staples are set in the slots 10.

The handle 57 of the drive 55 is fastened on the jaw 5 by means of the bent tongues 60 (FIG. 11), situated in the longitudinal slots 61 of the jaw 5. For excluding the inadvertent movement of the drive 55 (FIG. 10) of the pushers 11, and, consequently, an accidental ejection of the staples from the magazine 9, the drive 55 has a resilient catch 62 (FIG. 12) interacting with the lug 63 on the jaw 5. The catch 62 reliably secures the drive 55 (FIG. 10) in the initial position. When it is necessary to move the drive 55, the operator disengages the catch 62 from the lug 63 and actuates the handle 57.

To provide convenient juxtaposition of the organs to be sutured when applying the first tier of sutures, the apparatus is provided with scales 64 (FIG. 3), on the face surface 65 of the toothed strip 19.

For applying the second tier of buried sutures, the proposed apparatus in one of the embodiments is provided with a device for burying the first tier of sutures. This device is made in the form of a fork 66 (FIGS. 13, 14 and 15), whose jaws 67 are situated between the jaws 3, 4, and 5, 6 (FIG. 16) of the clamps 1 and 2. The fork 66 (FIG. 14) is intended for encompassing the sutured organs along the first tier of sutures and disposing it at the moment of applying the second tier of sutures together with the sutured organs encompassed by said fork, between the jaws 3, 4, and 5, 6 (FIG. 16) of the clamps 1 and 2. The longitudinal axis of the fork 66 (FIG. 14) is approximately parallel to the longitudinal axis of the apparatus, and the length of the jaws 67 corresponds to the length of the magazine 9 and the die 12.

Jaws 67 of the fork 66 may be of a circular shape 68 in cross-section (see FIG. 17) or in the form of a segment (not shown in the drawing). This shape of the cross-section for the jaws 67 is condusive to burying the inverted sutures 69 relative to the lumen of the organs.

The jaws of the fork may have a U-shaped cross-section, as, for example, the jaws 70 (FIG. 18), with their channels 71 facing each other. Such a cross-section of the jaws 70 is condusive to burying everted sutures 72 relative to the lumen of the organs. However, the convex shape of the jaws 67 (FIG. 16) can also be used when burying everted sutures 72.

In the represented embodiment of the apparatus the jaws 67 of the fork 66 (FIG. 14) are resilient and are provided with a locking member 73, preventing the divergence of their tips at the moment of burying the first tier of sutures and applying the second tier of sutures. With the locking member 73 removed, the tips of the jaws 67 are slightly divergent, as shown in FIG. 15.

The locking member 73 (FIG. 19) is made in the shape of a frame with a rectangular window 74, whose width corresponds to that of the jaws 67.

Recesses 75 are provided on the jaws 67 of the fork 66 for securing the locking member 73 (FIG. 15). The jaws 67 have different length, and the locking member 73 (FIG. 19) is provided with lugs 76 for conveniently mounting it on the jaws 67 during the compression of the sutured organs along the line of the first tier of sutures and for removing the locking member 73 following the application of the second tier of sutures.

In the variant represented in the Figures the embodiment of the fork 66 (FIGS. 14 and 15) ensures the atraumatic burying of the first tier of sutures when applying the second tier, and atraumatic removal of the fork 66 following the suturing of the organs.

This embodiment does not rule out the possible use of other advisable variants of embodying the fork 66 and the locking member 73. For example, the jaws of the fork may be made rigid. In this case the fork can be used without the locking member linking the free tips of the jaws.

The prongs of the fork may be connected also by means of a hinge on one side and a locking member on the other (not shown).

Instead of a special locking member for connecting the jaws of the fork a conventional soft ligature (for example silk thread) may be used, to be tied in a knot, and dissected and removed after the placement of the second tier of sutures. The recesses 75 (FIG. 15) on the jaws 67 of the fork 66 serve in this case for securing the ligature.

The end of the fork 66 opposite to the jaws 67 (FIGS. 13 and 14) is made in the form of a plate 77 with an opening 78 (FIG. 14) and a slot 79. The plate 77 is fixed on a pin 80, set immovably on the jaw 6 of the clamp 2. The pin 80 is made with an annular groove 81 (FIG. 20) interacting with the hole 78 of the plate 77 and fixing the fork 66 (FIG. 14) relative to the jaws of the clamps 1 and 2. The plate 77 is disposed in the annular groove 88 (FIG. 20) with some free play crosswisely giving the fork 66 (FIG. 13) the possibility of small crosswise movements relative to the jaws 1 and 2. The plate 77 also has an elongated opening 82 (FIG. 14). Set in the opening 82 is a pin 83, secured on the jaw 6 and supporting the fork 66 approximately parallel relative to the longitudinal axis of the clamp 2.

The fork for burying the first tier of sutures does not have to be connected with the clamp jaws. In this case it appears as a bent resilient yoke 81 (FIG. 21), whose prongs 85 are connected with a locking member 73. In the process of applying the second tier of sutures, the prongs 85 of the yoke 84, set along the first tier of sutures on the sutured organs, are disposed between the clamps 1 and 2 (FIG. 22) as represented in FIGS. 16 and 22.

The performance of the apparatus will now be described for the following methods of its application:

(a) when placing sutures everted relative to the cavity of the organ with contact of the inner surfaces of the walls of the organs, for example, of the mucous membrane when suturing intestines;

(b) when suturing the walls of organs end-to-end with contact of the walls along the surface of the section;

(c) when suturing the walls of organs with a suture inverted relative to the cavity of the organs with contact of the outer surface of the walls of the organs and the disposal of the staples of the suture on the outside relative to the cavity of the organs;

(d) when suturing the walls of organs with a two-tier buried suture (first variant);

(e) when suturing the walls of organs with a two-tier buried suture making use of the fork for burying the first tier of sutures (second variant);

(f) when suturing the lumen of organs in a multi-row, for example, two-row suture;

(g) when suturing the remaining portion of an organ and the portion to be removed with dissection of the organ between the rows of sutures applied;

(h) when suturing two remaining ends of an organ situated at some distance from each other; and (i) when suturing a lateral portion of an organ.

A detailed description of the interaction of the parts of the apparatus is given only when describing methods of applying everted sutures and when additional explanations are required to describe other methods. In other cases for the sake of simplicity, only the sequel of manipulations necessary for the implementation of these methods is noted.

The performance of the surgical apparatus for suturing organs with metal staples in the "end-to-end", "end-to-side", and "side-to-side" methods is of the same type. The only difference is that, depending on the pattern of suturing, an "end" of an organ (FIG. 23a) or its lateral portion (not shown in FIG. 23a) is clamped and fixed between the jaws of the clamps, for example, by the jaws 5 and 6 of the clamp 2.

We therefore further describe the method of suturing organs only according to the "end-to-end" pattern.

Before using the apparatus the clamps 1 and 2 (FIG. 1) are separated for which the cam 42 is turned into the initial position so that the working surface 45 (FIG. 9) of the cam 42 is disengaged from the pin 44, the clamps 1 and 2 are separated by turning them relative to the joint 46 (FIG. 1), and the clamp 2 is moved relative to the clamp 1 parallel to the axis of the joint 46.

The magazines 9 (FIG. 2) charged with staples (not shown in FIG. 2) are mounted in the jaws 4 and 5 of the clamps 1 and 2. The drive 55 (FIG. 10) of the pushers 11 and strip 28 (FIG. 5a), whose rests 29 lock the casings 15 in the forward position (FIG. 5b), are set in the extreme backward position, while the guides 38 lock the strips 20 (FIGS. 5b, 5c) with the bent teeth 18 locked in the initial position.

For making, for example, intestinal anastomoses, one of the portions to be sutured 86 (FIG. 23a) is disposed between the jaws of one of the clamps, for example, the jaws 5 and 6 of the clamp 2, so that said portion is disposed within the limits of the scale 64. Then, the walls of the organ are clamped. The free end 53 (FIG. 3) of the resilient lock 51 will at this moment close the jaws 5 and 6 of the clamp 2, setting, depending on the thickness of the walls, on one of the stepped recesses 54 of the jaw 5.

By moving the strips 28 of the two jaws 5 and 6 of the clamp 2 as far as they go, the movable strips 20 with the bent teeth 18 (FIG. 6c) are simultaneously moved by means of guides 38 (FIG. 6a) relative to the strips 19 with the straight teeth 17. As a result, the walls of the clamped organ will be grasped by the paired fixing teeth 17 and 18. The free end 33 (FIGS. 6a, 6b) of the spring-loaded plates 32 will be disposed opposite the slot 36 of the casing 15 and the rests 29 will unlock the casing 15.

Thereupon, by moving a scalpel along the surfaces 65 (FIG. 23a), the portion of the area to be sutured 86 is dissected for removal as shown in FIG. 23b.

In accordance with the disposal of the first portion to be sutured 86 relative to the scale 64 (FIG. 23a), the second portion 87 to be sutured is arranged on the jaws 5 and 6 of the clamp 2, according to a similar scale 64 (FIG. 23c) of the clamp 1.

Further, the walls of the second portion 87 to be sutured are fixed and the part of the organ to be removed is dissected as shown in FIG. 23d. The interaction of the components of the clamp 1 at this period of the operation is the same as when fixing the walls of the organ by means of the clamp 2 (FIGS. 23a, 23b).

By actuating with the fingers of the hand the movable casings 15 of each of the clamps, for example, the clamp 2, in the cross-wise direction, the casings 15 are set in the backward position, as shown in the Figure (FIGS. 7b and 23e, 23f). In the process of movement from the forward to the backward position, the casing 15 meets the inclined free end 33 (FIG. 6b) of the spring-loaded plate 32 and lifts it. After setting the casing 15 in the backward position, the end 33 (FIG. 7b) drops into the slot 36 of the casing 15, locking it is said position. The fixing teeth 17 and 18 (FIGS. 23e, 23f) at this moment separate the edges of the portions 86 and 87 to be sutured and maintain them in this state.

Then, the two clamps 1 and 2 are joined for which the axis and opening of the joint 46 (FIG. 1) are brought into coincidence. The jaws of the clamps 1 and 2 are brought together so that the forks 47, secured on the jaws of the clamp 2, will encompass the jaws of the clamp 1, and the lugs 48 will enter the slots 49. The cam 42 is turned, linking the clamps 1 and 2 together and setting the separated edges of the portions 86 and 87 (FIG. 23g) into the position for suturing between the magazines 9 and the dies 12. Depending on the thickness of the walls of the organs to be sutured and their properties, the cams 42 (FIG. 1) are turned through a certain angle, setting the necessary suturing clearance between the magazines 9 (FIG. 23g) and the dies 12.

The resilient catch 62 (FIG. 10) of the drive 55 of the pushers 11 of each of the clamps is disengaged from the lug 63 and by actuating the handle 57 the wedge 56 is inserted into the opening 59 of the magazine 9. The wedge 56 shifts the pushers 11, which eject the staples 88 (FIGS. 23e, 23f) from the slots 10 (FIG. 23g) of the magazines 9. Having pierced the walls of the organs and being clinched against the grooves 13, the bent staples 88a suture the separated edges of the walls along the semiperimeters disposed between the jaws 3, 5 and 4, 6 of the clamps 1 and 2.

After that the strips 28 (FIG. 8a) are drawn backward as far as they will go, separating the paired fixing teeth 17 and 18 (FIG. 8c) and releasing the walls of the organs.

Simultaneously with the drawing back of the strips 28 (FIG. 8a), the free ends 33 of the spring-loaded plates 32 are withdrawn from the grooves 36 of the casings 15, releasing them from being locked in the backward position.

Then, the cam 42 (FIG. 9) is set in the initial position, somewhat parting the jaws of the clamps 1 and 2. The end 53 of the resilient locks 51 are disengaged from the stepped recesses 54 (FIG. 3) and the upper jaws 3 and 5 (FIG. 2) of the clamps 1 and 2 are drawn apart from the lower ones 4 and 6.

The lower pairs of jaws 4 and 6 of the clamps 1 and 2 are withdrawn from under the sutured organs.

The described suturing process results in a suture 89 (FIG. 24) everted relative to the cavity of the organs with contact of the walls of the inner surface, for example, the mucous membrane, when suturing intestines.

Due to the fact that the embodiment of the apparatus provides for the separation of the edges of the portions 86 and 87 to be sutured (FIGS. 23e, 23f) and for their fixation in the separated position prior to the joining of the clamps 1 and 2, the precision and reliability of the juxtaposition of the edges of the walls in the suture are enhanced.

When suturing the walls of organs end-to-end with contact of the walls along the surface of the section following the clamping of the portions to be sutured as shown in FIGS. 23a, 23c and the fixation of the walls of the organs, the portion of the organs to be removed is dissected at a small distance (2-4 mm) from the frontal surface 65. As a result the section 90 (FIGS. 25a, 25b) of the walls of the portions 91 and 92 to be sutured is disposed at the appropriate distance relative to the fixing teeth 17 and 18.

Then, the casings 15 (FIGS. 25c, 25d) of the clamps 1 and 2 are set in the backward position, separating thereby the fixed edges of the portions 91 and 92 to be sutured. The clamps 1 and 2 (FIG. 25e) are joined together and the jaws 3, 5 and 4, 6 are brought together until contact by a small compression of the edges 93 of the walls of the organs disposed between the section 90 and fixing teeth 17 and 18.

By means of a flat plate 94 (or any suitable instrument, for example, the handle of a scalpel), which is introduced between the casings 15 of the juxtaposed jaws 3, 5 and 4, 6 of the clamps 1 and 2, the edges 93 of the walls of the organs are sunk into the zone between the magazines 9 and the dies 12.

The suturing clearance is set according to the thicknesses of the juxtaposed walls and they are sutured as shown in FIG. 25f.

The result of the described suturing process is an end-to-end suture 95 (FIG. 26) with contact of the sutured walls along the surface of the section 90.

When suturing the walls with a suture 96 (FIG. 27) inverted relative to the cavity of the organs with contact of the walls of the outer surface and the arrangement of the staples 88a of the suture externally relative to the cavity of the organs, for example, when suturing intestines with contact of the walls' serous membranes, the same manipulations are carried out as when suturing the walls of organs end-to-end by means of the clamps 1 and 2 (FIGS. 25a-25f) of the apparatus and the plate 94 (FIG. 25e). The only difference is that the distance from the section of the tissues when dissecting the part of the organs to be removed to the frontal surface 65 (FIG. 23a) must be somewhat larger, than when suturing the walls end-to-end, for example, 5-7 cm, and this is determined by the surgeon depending on the actual thickness of the walls of the organs concerned.

Figure 28A:
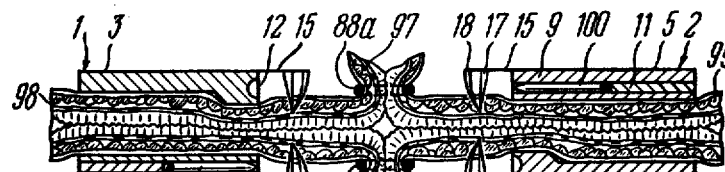
FIG. 28a, b, c and d are schematic representations of the main stages in applying the second tier of buried sutures by means of the apparatus in accordance with the invention.

When suturing organs with a two-tier buried suture by means of the apparatus, represented in FIG. 1, at some distance (for example 3-6 mm) from the line of the first tier 97 (FIG. 28a) of the suture, applied by hand or by means of an apparatus according to one of the described methods (see, for example, FIGS. 23 and 24), the walls of the organ 98 (FIG. 28a) are clamped by the jaws 3 and 4 of the clamp 1 and those of the organ 99 with the jaws 5 and 6 of the clamp 2, whose magazines 9 are charged with staples 100.

The walls are fixed by their external layers with the fixing teeth 17 and 18.

Figure 28B:

The casings 15 are set in the backward position as shown in FIG. 28b. The clamps 1 and 2 are joined and the mating jaws 3, 5 and 4, 6 are brought together so that the first tier 97 of the suture is displaced closely (not shown in FIG. 28) between the casings 15.

After that the free end 53 (FIG. 3) of the resilient locks 51 is disengaged from one of the recesses 54 simultaneously on both the clamps 1 and 2 (FIG. 1) wherein it was situated when the organs were compressed. The jaws 3 and 5 (FIG. 28c) are drawn away from the jaws 4 and 6 of the clamps 1 and 2 over some distance at which the free end 53 (FIG. 3) of the resilient locks 51 will engage with another of the recesses 54, providing for a clearance between the jaws 3, 5 and 4, 6, greater than during the initial compression of the walls of the organs.

Figure 28C:
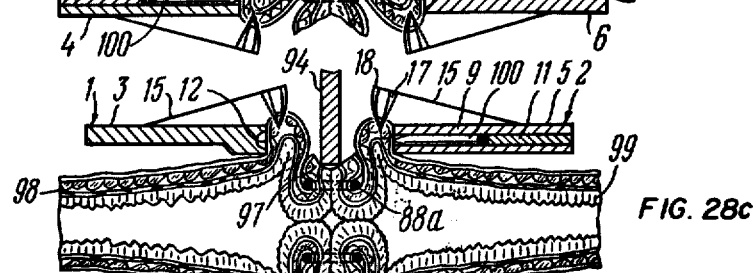
Figure 28D:
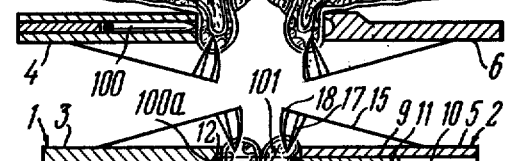

The first tier 97 of the suture is buried by means of the flat plate 94 (FIG. 28c). The jaws 3, 5 4, 6 of the clamps 1 and 2 juxtaposed during suturing are brought together as shown in FIG. 28d and are joined by means of the cam 42 (FIG. 1), while adjusting the necessary suturing clearance between the magazines 9 (FIG. 28d) and the dies 12 in accordance with the thickness of the compressed walls.

The external layers of the walls are sutured with staples 100a, having thus applied the second buried tier 101 of the suture.

Then the walls of the organs are released from fixation, the cam 42 (FIG. 1) is turned into the initial position, thereby separating the clamps 1 and 2, and the jaws 3 and 5 (FIG. 28d) are drawn away from the jaws 4 and 6 of the clamps 1 and 2.

Figure 29:
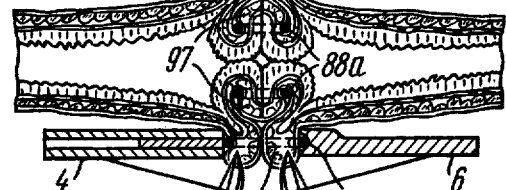
FIG. 29 shows a cross-section of a two-tier buried suture, applied with the aid of the apparatus of the invention.

The described process of suturing the walls of organs by means of the apparatus, according to the invention, represented in FIG. 1, results in a two-tier buried suture 102 (FIG. 29).

Figure 30A:
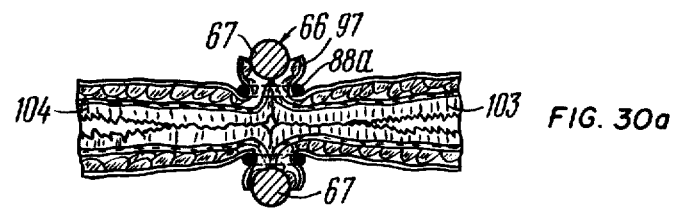
FIGS. 30a, b, c, d, e and f are schematic representations of the main stages in placing the second tier of buried sutures by means of the apparatus with a device for burying the first tier of sutures.

For suturing organs with a two-tier buried suture by means of the apparatus, according to the invention, shown in FIG. 13 the jaws 67 (FIGS. 15 and 30a) of the fork 66, preliminarily separated from the corresponding clamp 2 (FIG. 14), are disposed along the first tier 97 (FIG. 30a) of the suture, applied, for example, according to the pattern depicted in FIG. 23. The jaws 67 are prevented from diverging by means of the locking member 73.

Figure 30B:
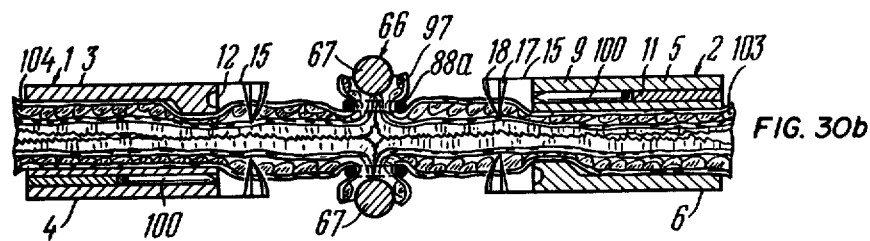

One of the sutured organs, for example organ 103 (FIG. 30b), is encompassed by the jaws 5 and 6 of the clamp 2 on one side relative to the jaws 67 of the fork 66, and said fork 66 (FIG. 14) is connected with the clamp 2, bringing the hole 78 of the plate 77 in coincidence with the annular groove of the pin 80, and the organ 103 is compressed at a distance of 4–7 mm from the jaws 67 (FIG. 30b) of the fork 66 and its walls are fixed by securing their outer layers.

Then the second of the sutured organs, organ 104, is embraced by the jaws 3 and 4 of the clamp 1 from the other side relative to the jaws 67 of the fork 66, the clamps 1 and 2 are joined by means of the joint 46 (FIG. 13) and the walls of the organs are fixed by engaging their external layers in the same way as was done by means of the clamp 2.

Figure 30C:
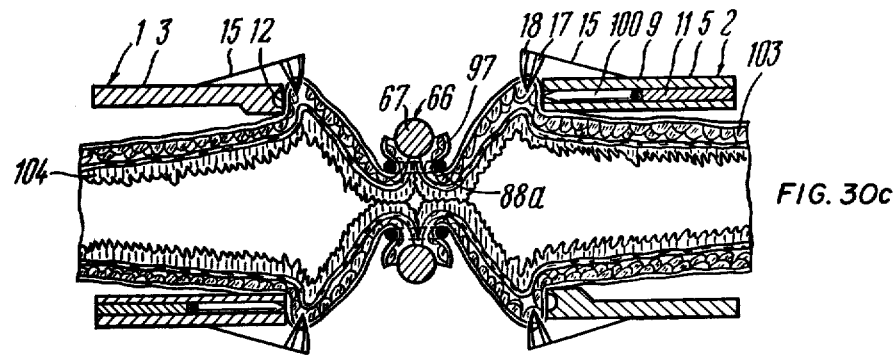

The casings 15 (FIG. 30c) are drawn into the backward position and the jaws 3, 5 and 4, 6 of the clamps 1 and 2 are opened by affecting the resilient locks 51 (FIG. 14).

Figure 30D:
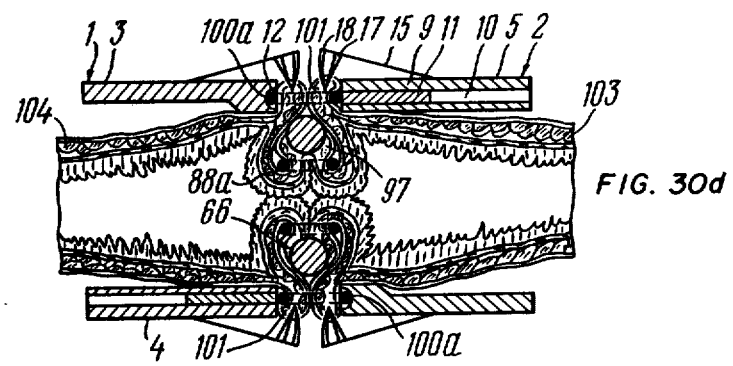

The jaws 3 an 5, and 4 and 6 (FIG. 30d) of the clamps 1 and 2 are joined by means of the cam 42 (FIG. 13), approximating the fixed areas until they touch and setting the required suturing clearance according to the thickness of the juxtaposed walls. When doing so the first tier 97 (FIG. 30d) of the suture compressed by the jaws 67 of the fork 66 is buried, while the external layers of the walls of the organs 103 and 104 are placed in the suturing position between the magazines 9 and the dies 12, encompassing the first tier 97 of the suture.

The juxtaposed walls of the organs 103 and 104 are sutured with the staples 100a, forming the second buried tier 101 of the suture.

Figure 30E:
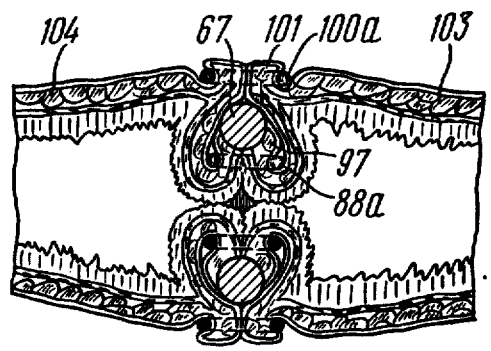
Figure 30F:
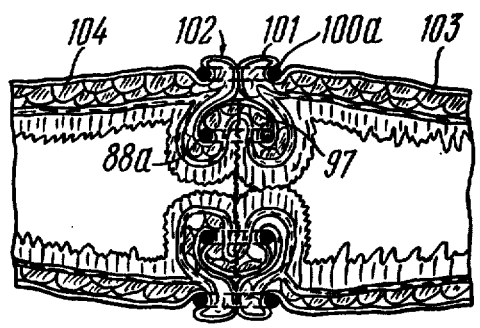
Figure 31:
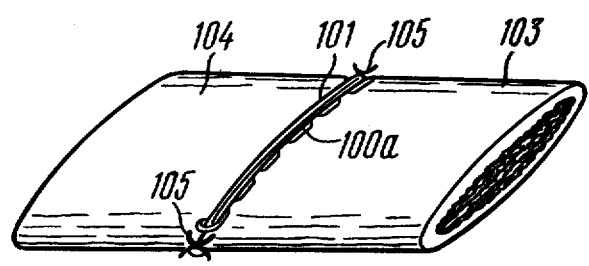
FIG. 31 is a fragmentary, perspective view of organs sutured with a two-tier buried suture by means of the apparatus of the invention.

After that the walls of the organs 103 and 104 are released from fixation, the jaws 3, 5 and 4, 6 of the clamps 1 and 2 are drawn apart and withdrawn together with the fork 66 or separately from the surgical wound, having preliminary disconnected the fork 66 from the clamp 2. In order the withdraw the fork 66 the locking member 73 is removed from the ends of its jaws 67 (FIG. 14) and said jaws 67 (FIG. 30e) are withdrawn from the space between the first 97 (FIG. 30f) and the second 101 tiers of sutures. At the points of convergence of the semiperimeters of the second tier 101 of the sutures, one-two buried interrupted sutures 105 (FIG. 31) are applied manually.

When using the resilient yoke 84 (FIG. 21) for burying the first tier 97 (FIG. 30a) of the suture, all the basic stages in placing the second tier 101 (FIG. 30f) correspond to the stages, represented in FIGS. 30a–30f. In distinction from the described previous methods of applying the second tier 101 of sutures by means of the fork 66, the utilization of the yoke 84 (FIGS. 21 and 22) makes it unnecessary to disconnect and connect the device for burying the first tier of the suture from and to the clamps 1 and 2. The prongs 85 of the yoke 84, set along the first tier 97 of the suture and secured by means of the locking member 73 or tied by means of a soft ligature, are disposed between the jaws 3, 4, 5 and 6 (FIGS. 30b, 30c, 30d) together with the organs to be sutured after their walls are grasped and fixed.

The utilization of the fork 66 (FIG. 15) or the yoke 84 (FIG. 21) for burying the first tier 97 (FIG. 30a) of the suture is advisable in cases when there is no cases approach to the first tier 97 of the suture for burying it with the aid of the plate 94 (FIG. 28c).

Figure 32:
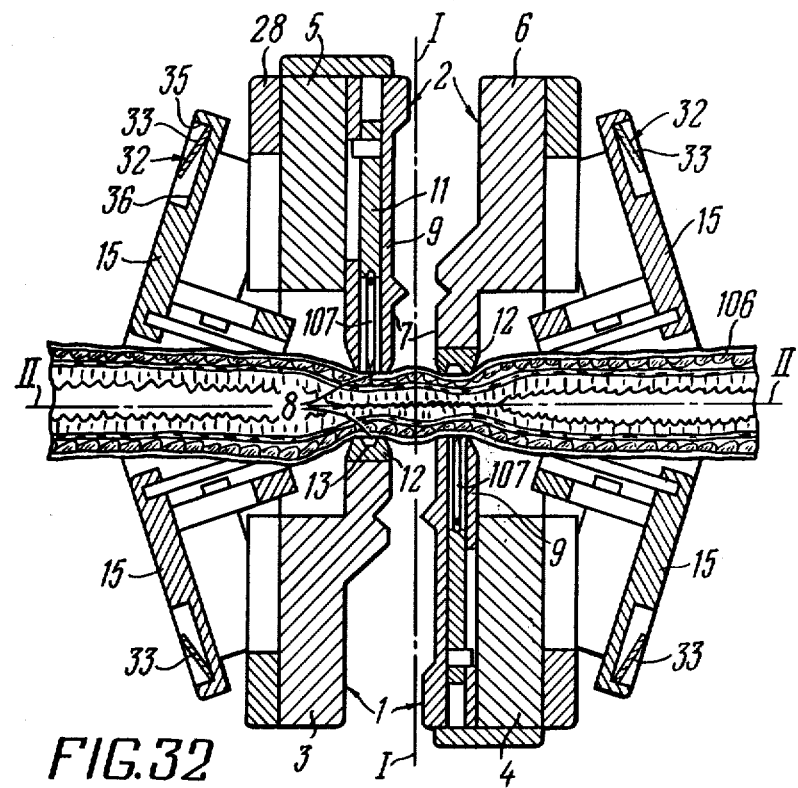
FIG. 32 is an enlarged cross-sectional view of the clamps in the zone of the magazines and dies of the apparatus of the invention, prepared for suturing an organ with the invention of completely closing a lumen.

When using the apparatus for the various methods of suturing organs for the purpose of completely closing a lumen the easily detachable toothed strips 19 and 20 are removed from the casings 15 (FIG. 2) of all the jaws 3, 4, 5 and 6 of the clamps 1 and 2, and the casings 15 are set in the backward position, as shown in FIG. 32, and are locked by means of the free ends 33 of the spring-loaded plates 32. Thereby the casings 15 are locked immovably on the jaws 3, 4 and 5, 6 of the clamps 1 and 2, and all the members of the casings 15 in the zone of the magazines 9 and the dies 12 are disposed behind the mating surfaces 8 of the clamps 1 and 2.

For suturing an organ with a two-row suture the jaws 3 and 4 of the clamp 1 and the jaws 5 and 6 of the clamp 2 are connected by means of the spring lock 51 (FIG. 3).

The jaws 3 and 4 of the clamp 1, are, for example, brought under the organ 106 to be sutured (FIG. 32) and the clamp 2 is connected with said clamp 1 by means of the joint 46 (FIG. 1). By rotating the clamp 2 relative to said joint 46, the jaws 5 and 6 (FIG. 32) are juxtaposed with the jaws 3 and 4 of said clamp 1 and said clamps 1 and 2 are connected by means of the cam 42 (FIG. 1) setting the suturing clearance between the magazines 9 (FIGS. 32 and 33) and the dies 12, to correspond to the thickness of the walls of the organ 106. By a motion of the drives 55 (FIG. 10) of the pushers 11 the staples 107 (FIG. 32) are ejected. As they are being bent, the clinched staples 107a (FIG. 33) suture the walls of the organ 106.

Then the cam 42 (FIG. 1) is set in the initial position, the jaws 5 and 6 (FIG. 33) of the clamp 2 are drawn away from the jaws 3 and 4 of the clamp 1 and the apparatus is withdrawn from the surgical wound.

Figure 34:
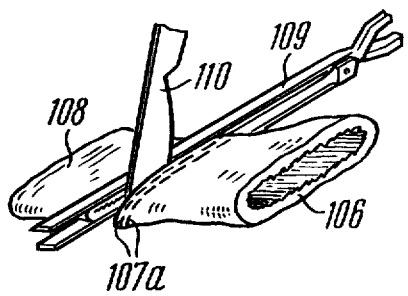
FIG. 34 shows an organ with a two-row suture, applied by the apparatus of the invention, and illustrating resecting a portion of the organ to be removed from a remaining portion.

A conventional known clamp 109 is placed on a portion 108 of the sutured organ 106 to be removed parallel to the row of the clinched staples 107a (FIG. 34) and the walls of the organs between the clamp 109 and staples 107a are dissected with a scalpel 110.

Figure 33:
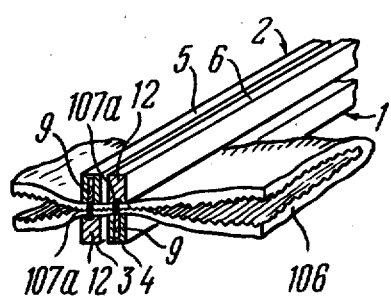
FIG. 33 is a fragmentary, perspective view showing of the clamps of the apparatus, according to the invention, at the moment of applying a multirow suture when suturing an organ.

When suturing by means of the apparatus, the organ's remaining portion 111 (FIG. 35), and the portion 112 to be removed with the resection of the organ between the applied rows of sutures, the walls of the organ are sutured with staples 107a, according to the patterns represented in FIGS. 32 and 33. Then, by moving the scalpel 110 (FIG. 35) between the jaws 3 and 5 and the jaws 4 and 6 of the clamps 1 and 2, the walls of the organ are dissected between said organ's remaining portion 111 and the portion 112 to be removed. Before compressing the organ to be sutured with the clamps 1 and 2, the jaws 3 and 4, and 5 and 6 must be somewhat parted, so that the scalpel 110 can be introduced between them for dissecting said organ as shown in FIG. 36.

When suturing the two remaining ends 113 (FIG. 37), and 114 of the organ, disposed at some distance from each other, the jaws 3 and 4 of the clamp 1 are parted by a distance corresponding to the selected areas for placing the sutures, and they are introduced beneath the organ to be resected. The jaws 5 and 6 of the clamp 2 are parted and the clamps 1 and 2 are joined by means of the joint 46 (FIG. 1) after which the jaws 3 and 4 of the clamp 1 and the jaws 5 and 6 of the clamp 2 are connected and the walls of the organ to be sutured are sutured with the staples 107a (FIG. 37). Two conventional known clamps 109 are placed on said organ's portion 115 to be removed parallel to the paired jaws 3 and 5 and 4 and 6 of the clamps 1 and 2, and the walls of the organ between the jaws of the accessory clamps 109 and the jaws 3 and 5, and the jaws 4 and 6 of the clamps 1 and 2 of the apparatus are dissected with the scalpel 110. Then, the organ's part 115 to be removed is withdrawn from the surgical wound together with the clamps 109 and the clamps 1 and 2 of the apparatus, leaving the ends 113 and 114 of the organ closed up by sutures, as best shown in FIG. 38.

When suturing a lateral portion of an organ between the pair jaws of the clamps of the apparatus, for example 3 and 5 (FIG. 39) of the clamps 1 and 2, the organ's lateral portion 116 is sutured up, and the portion 117 to be removed is cut off. After opening the jaws 3 and 5 and removing the clamps 1 and 2 there remains said organ's lateral portion 116 sutured with the staples 107a (FIG. 40).

A special feature of using the apparatus, according to the invention, in all the above described methods of suturing organs (FIGS. 32 to 40) is that organs are compressed in the mating plane II—II (FIG. 32) of the clamps 1 and 2, whereas when making anastomoses (FIGS. 23 to 31) they are compressed in the mating planes I—I (FIG. 2) of the jaws 3, 4, 5 and 6 of each of the clamps 1 and 2.

What is claimed is:

1. A surgical apparatus for suturing organs, such as intestines, stomach, vessels and the like, with metal staples in the end-to-end, end-to-side and side-to-side methods, with the working part of the apparatus disposed outside of the organs being sutured, comprising: two clamps; two jaws of each of said clamps for fixing one of the organs being sutured therebetween, said clamps being detachably joined together so that when joined the mating plane of said jaws of each of said clamps is perpendicular to the mating plane of said clamps; two magazines with slots for staples, each of said magazines being mounted on one of said jaws of each of said clamps; pushers for pushing out said staples from said magazine slots; two dies with grooves for clinching said staples, each of said dies disposed on one of said clamp jaws so that said magazines and dies interacting with each other during suturing are situated on the jaws of different clamps; means for grasping and fixing the walls of the organs being sutured; four casings of said means, fastened on said jaws, one of said casings being fastened to each of said jaws; members for grasping and fixing the walls of said organ or organs, situated on said casings and directed along said jaws; guides made within said jaws, ensuring the fastening therein of said casings with the provision for limited movement of each of said casings in a plane, perpendicular to the mating plane of said jaws and the mating plane of said clamps, so that each of said casings may be set to either one of two extreme positions of which the forward extreme position corresponds to the moment of clamping and grasping the walls of the organs being sutured, whereby said fixing members lie between the mating surfaces of said jaws of said clamps and at some distance in front of the mating surfaces of said clamps in their separate state, and in the backward extreme position in which said fixing members lie at some distance from the mating surfaces of said clamp jaws and approximately within the mating surfaces of said clamps; locks locking said casings in said forward position, mounted on said jaws; and locks locking said casings in said backward position, mounted on said jaws and retaining said jaws regardless of the reciprocal position of said jaws and the suturing clearance width between said magazines and said dies.

2. A surgical apparatus as claimed in claim 1, with said guides of said movable casings comprising closed slots, provided in said clamp jaws, having inclined portions in which are displaced cylindrical pins secured to said casings; and said locks of said movable casings, locking said casings in the rear position, comprising spring-loaded plates secured in a cantilever fashion to said clamp jaws and engaging with their free ends shoulders provided on said movable casings.

3. A surgical apparatus as claimed in claim 2, in which said free ends of said spring-loaded plates are inclined to the mating plane of the clamp jaws, said shoulders being formed by the wall of open slots made in said casings, and which has common strips, serving to secure therein said locks locking said casings in the forward and backward positions, movably set along each said clamp jaw and occupying one of two extreme positions, in one of which the casings are locked in the forward position, and in the other the casings are locked in the backward position, and the length of the working portion of each of said spring-loaded plates interacting with said open slots is shorter than the run of said common strips.

4. A surgical apparatus as claimed in claim 3, comprising a means for changing the distance between the mating surfaces of said clamps, and linking the jaws of one of said clamps, with those of the other clamp.

5. A surgical apparatus as claimed in claim 2, comprising a means for changing the distance between the mating surfaces of said clamps, and linking the jaws of one of said clamps with those of the other clamp.

6. A surgical apparatus as claimed in claim 3, comprising means for changing the distance between mating planes or surfaces of said clamps, linking the jaws of one of said clamps with those of the other clamp.

7. A surgical apparatus as claimed in claim 4, comprising a detachable joint, connecting the ends of said clamps; a rotating cam of said means for changing the distance between the mating surfaces of the clamps, secured on one of said joints, the working surface of said cam having the configuration of a portion of a diverging spiral with an angle of helix not greater than the angle of selfbreaking; and a pin fastened on the other said clamp and interacting with said rotatable cam.

8. A surgical apparatus as claimed in claim 6, comprising a detachable joint, connecting the ends of said clamps; a rotatable cam of said means for changing the distance between the mating surfaces of said clamps, fastened on one of said joints, the working surface of said cam having the configuration of a portion of a diverging spiral with an angle of helix not greater than the angle of self-breaking; and a pin fastened on the other said clamp and interacting with said rotatable cam.

9. A surgical apparatus as claimed in claim 7, in which said rotatable cam is fastened approximately in the medium part of the clamp between said detachable joint and said means for grasping and fixing the walls of the organs being sutured, and is secured on the ends of the clamp opposite to the joint.

10. A surgical apparatus as claimed in claim 8, in which said rotatable cam is secured approximately in the medium part of the clamp between said detachable joint, and said means for grasping and fixing the walls of the organs being sutured, and is fastened on the ends of the clamp opposite to the joint.

11. A surgical apparatus as claimed in claim 1, comprising a device for burying a first tier of sutures connecting the organs when placing a second tier of sutures, made as a fork, intended for encompassing the sutured organs along the fist tier of sutures and for disposing it at the moment of placing the second tier of sutures, together with the sutured organs encompassed therewith, between said clamp jaws so that the longitudinal axis thereof is approximately parallel to the longitudinal axis of said surgical apparatus, and said fork having jaws, whose length corresponds to the length of said magazines and said dies.

12. A surgical apparatus as claimed in claim 10, comprising a device for burying a first tier of sutures, connecting the organs when placing a second tier of sutures, made as a fork, intended for encompassing the sutured organs along the first tier of sutures and for disposing it at the moment of placing the second tier of sutures, together with the sutured organs encompassed therewith, between said clamp jaws so that its longitudinal axis is approximately parallel to the longitudinal axis of said surgical apparatus, and said fork having jaws, whose length corresponds to the length of said magazine and said die.

13. A surgical apparatus as claimed in claim 11, in which said fork jaws have a round or circular cross-section.

14. A surgical apparatus as claimed in claim 11, in which said fork jaws are U-shaped in cross-section and whose channels face each other.

15. A surgical apparatus as claimed in claim 11, in which said fork jaws are resilient and have a detachable locking member, preventing the divergence of their tips at the moment of burying the first tier of sutures and placing the second tier of sutures.

16. A surgical apparatus as claimed in claim 15, in which recesses are made on the tips of said jaws of said fork for securing said locking member.

17. A surgical apparatus as claimed in claim 15, in which said locking member is made in the form of a frame with a rectangular window.

* * * * *